(12) United States Patent
Sughrue et al.

(10) Patent No.: US 11,145,119 B2
(45) Date of Patent: Oct. 12, 2021

(54) DIFFERENTIAL BRAIN NETWORK ANALYSIS

(71) Applicant: Omniscient Neurotechnology Pty Limited, Sydney (AU)

(72) Inventors: Michael Edward Sughrue, Sydney (AU); Stephane Philippe Doyen, Glebe (AU)

(73) Assignee: Omniscient Neurotechnology Pty Limited, Sydney (AU)

( * ) Notice: Subject to any disclaimer, the term of this patent is extended or adjusted under 35 U.S.C. 154(b) by 0 days.

(21) Appl. No.: 17/066,178

(22) Filed: Oct. 8, 2020

(65) Prior Publication Data
US 2021/0118226 A1    Apr. 22, 2021

(30) Foreign Application Priority Data

Oct. 18, 2019    (AU) ................................ 2019903933

(51) Int. Cl.
*G06T 17/20* (2006.01)
*G01R 33/56* (2006.01)
(Continued)

(52) U.S. Cl.
CPC ............ *G06T 17/20* (2013.01); *A61B 5/0042* (2013.01); *A61B 5/055* (2013.01);
(Continued)

(58) Field of Classification Search
CPC ..... A61B 5/055; A61B 2090/374; A61B 5/40; A61B 5/0042; G01R 33/20;
(Continued)

(56) References Cited

U.S. PATENT DOCUMENTS 9,519,984 B2    12/2016 Masuko
2010/0004527 A1*  1/2010 Dale ................. G01R 33/56341
                                                            600/410
(Continued)

FOREIGN PATENT DOCUMENTS

WO    WO 2001/038895    5/2001
WO    WO 2016/083927    1/2017
WO    WO 2019/100032    5/2019

OTHER PUBLICATIONS

Moreno-Dominguez 2014 Ph.D. Thesis in Engineering, Max Planck Institute for Human Cognitive and Brain Sciences Leipzig Germany, 188 pages (Year: 2014).*

(Continued)

*Primary Examiner* — Michael J Tsai
*Assistant Examiner* — Patrick M Mehl
(74) *Attorney, Agent, or Firm* — Fish & Richardson P.C.

(57) ABSTRACT

A system and method of generating a graphical representation of a network of a subject human brain. The method comprises receiving, via a user interface, a selection of the network of the subject brain; determining, based on an MRI image of the subject brain and one or more identifiers associated with the selection, one or more parcellations of the subject brain (405); determining, using three-dimensional coordinates associated with each parcellation, corresponding tracts in a diffusion tensor image of the brain (425); and generating a graphical representation of the selected network (430), the graphical representation including at least one of (i) one or more surfaces representing the one or more parcellations, each surface generated using the coordinates, and (ii) the determined tracts.

22 Claims, 15 Drawing Sheets

(51) Int. Cl.
    *G01R 33/563*     (2006.01)
    *G16H 30/40*     (2018.01)
    *A61B 5/055*     (2006.01)
    *A61B 5/00*     (2006.01)
    *G16H 50/50*     (2018.01)

(52) U.S. Cl.
CPC ... *G01R 33/5608* (2013.01); *G01R 33/56341* (2013.01); *G16H 30/40* (2018.01); *G16H 50/50* (2018.01); *G06T 2200/24* (2013.01); *G06T 2210/41* (2013.01)

(58) Field of Classification Search
CPC .......... G01R 33/56341; G01R 33/5608; G06T 17/20; G06T 2200/24; G06T 2210/41; G16H 50/50; G16H 30/40
See application file for complete search history.

(56) References Cited

U.S. PATENT DOCUMENTS

| | | | |
|---|---|---|---|
| 2011/0016432 A1* | 1/2011 | Helfman | G06T 11/206 715/843 |
| 2016/0307316 A1* | 10/2016 | Miller | A61B 5/4064 |
| 2017/0035320 A1* | 2/2017 | Verma | G06T 7/187 |
| 2017/0052241 A1 | 2/2017 | Cetingul et al. | |
| 2017/0076452 A1* | 3/2017 | Yui | G06T 7/11 |
| 2017/0285124 A1* | 10/2017 | Verma | G01R 33/5608 |
| 2018/0018790 A1* | 1/2018 | Lachner | G06T 7/11 |

OTHER PUBLICATIONS

Petrovic et al. 2011 Med. Image Comput. Comput. Assist. Interv. 14: 524-531 (Year: 2011).*
Lin et al. 2007 ISBRA 2007 LNBI 4463 pp. 539-550; Mandoiu et Zelikovsky (Eds.) (Year: 2007).*
Li et al. 2017 Frontiers in Neuroinformatics 11:1-13 (Year: 2017).*
Daducci et al. 2012 PLoS ONE 7:e48121 9pages (Year: 2012).*
Hosseini et al. 2012 PLoS ONE 7:e40709 pp. 1-15 (Year: 2012).*
Stanford University 2014 Gat Analysis Toolbox; internet address cbrian.stanford.edu/GAT_MANUAL 46 pages (Year: 2014).*
Muthusami et al. 2014 J. Magn. Reson. Imag. 40:1041-1053 (Year: 2014).*
Rojas et al. 2016 Frontiers in NeuroInformatics 10 article 40 6 pages (Year: 2016).*
LaPlante et al., "The Connectome Visualization Utility: Software for Visualization of Human Brain Networks," PLoS One, Dec. 2014, 9((12):1-18.
Urchs et al., "MIST: A multi-resolution parcellation of functional brain networks," MNI Open Research, Dec. 5, 2017, 1(3):1-30.
Xia et al., "BrainNet Viewer: A Network Visualization Tool for Human Brain Connectomics," PLoS One, Jul. 2013, 8(7):1-15.
PCT International Search Report and Written Opinion in International Appln. No. PCT/AU2020/051092, dated Nov. 26, 2020, 10 pages.

* cited by examiner

DIFFERENTIAL BRAIN NETWORK ANALYSIS

CROSS-REFERENCE TO RELATED APPLICATIONS

This application claims priority to Australian Provisional Patent Application No. 2019903933 entitled "System and Method for Displaying a Network of a Brain," listing Michael Sughrue and Stephane Doyen as inventors and filed Oct. 18, 2019, the contents of which are incorporated herein in its entirety.

This application is related to U.S. patent application entitled "Brain Image Processing" listing Stephane Doyen, Charles Teo and Michael Sughrue as inventors and filed on the same day as the present application and incorporated by reference herein in its entirety.

FIELD

The present invention relates generally to reproducing or displaying images of a human brain, and in particular to displaying a graphical representation of a network of a human brain including structural and functional connections of the network based on captured image data. The present invention also relates to a system, method and apparatus for displaying a graphical representation of a network of a human brain, and to a computer program product including a computer readable medium having recorded thereon a computer program for displaying a graphical representation of a network of a human brain.

BACKGROUND

Diffusion tensor imaging (DTI) uses magnetic resonance images to measure diffusion of water in a human brain. The measured diffusion is used to generate images of neural tracts and corresponding white matter fibers of the subject brain. Images captured using DTI relate to the whole brain and are correspondingly complex.

Neurosurgeons typically view visual representations of DTI images for a particular purpose, for example to study operation of a certain region of the brain, study effects of certain conditions on the brain or to plan for surgery.

A region of the brain can include millions of fibers gathered as tracts. However, users (such as neurosurgeons) typically require greater granularity in terms of operation and connections of the brain, such as identifying which tracts or fibers are connected or related. Without access to improved granularity, a neurosurgeon's study of the brain can be complex and may lead to risk in terms of identifying: 1) one or more of conditions present in the brain; 2) relevant areas for surgery; and 3) interactions between different components of the brain.

SUMMARY OF INVENTION

It is an object of the present invention to substantially overcome, or at least ameliorate, one or more disadvantages of existing arrangements.

According to one aspect of the present invention there is provided a method of generating a graphical representation of a network of a subject human brain, including: receiving, via a user interface, a selection of the network of the subject brain; determining, based on an MRI image of the subject brain and one or more identifiers associated with the selection, one or more parcellations of the subject brain; determining, using three-dimensional coordinates associated with each parcellation, corresponding tracts in a diffusion tensor image of the brain; and generating a graphical representation of the selected network, the graphical representation including at least one of (i) one or more surfaces representing the one or more parcellations, each surface generated using the coordinates, and (ii) the determined tracts. A network can be interconnections of particular tracts and fibers corresponding to a particular function or structure of the brain (such as language or hearing).

According to another aspect of the present invention there is provided a system, including: an image capture device configured to capture an MRI image and a diffusion tensor image of a subject human brain; a memory; and a processor, wherein the processor is configured to execute code stored on the memory for implementing a method of generating a graphical representation of a network of the subject human brain, the method including: receiving, via a user interface, a selection of the network of the subject brain; determining, based on the MRI image of the subject brain and one or more identifiers associated with the selection, one or more parcellations of the subject brain; determining, using three-dimensional coordinates associated with each parcellation, corresponding tracts in the diffusion tensor image of the brain; and generating a graphical representation of the selected network, the graphical representation including at least one of (i) one or more surfaces representing the one or more parcellations, each surface generated using the coordinates, and (ii) the determined tracts.

According to another aspect of the present invention there is provided a non-transitory computer readable medium having a computer program stored thereon to implement a method of generating a graphical representation of a network of a subject human brain, the program including: code for receiving, via a user interface, a selection of the network of the subject brain; code for determining, based on an MRI image of the subject brain and one or more identifiers associated with the selection, one or more parcellations of the subject brain; code for determining, using three-dimensional coordinates associated with each parcellation, corresponding tracts in a diffusion tensor image of the brain; and code for generating a graphical representation of the selected network, the graphical representation including at least one of (i) one or more surfaces representing the one or more parcellations, each surface generated using the coordinates, and (ii) the determined tracts.

According to another aspect of the present invention there is provided an apparatus configured to implement a method of generating a graphical representation of a network of a subject human brain, including: a memory; and a processor, wherein the processor is configured to execute code stored on the memory for: receiving, via a user interface, a selection of the network of the subject brain; determining, based on an MRI image of the subject brain and one or more identifiers associated with the selection, one or more parcellations of the subject brain; determining, using three-dimensional coordinates associated with each parcellation, corresponding tracts in a diffusion tensor image of the brain; and generating a graphical representation of the selected network, the graphical representation including at least one of (i) one or more surfaces representing the one or more parcellations, each surface generated using the coordinates, and (ii) the determined tracts.

The subject matter described in this specification can be implemented in particular embodiments to realize one or more of the following advantages. Current interfaces can be of limited clinical assistance in that such interfaces display too many tracts to be useful. Users of the interfaces such as neurosurgeons face difficulty in determining which tracts are connected and relevant to particular functions. Accordingly, particular tracts cannot be identified based on structure or function and the image of the region of interest may not be clinically meaningful. Quality of patient care and complexity of diagnosis and surgery can be adversely affected. Allowing a user to specify and visualize particular functions and/or structures of interest, 1) improves quality and speed of care, 2) improves surgical planning as the system highlights important/relevant networks, and 3) allows for finer determination of head trauma based on a scan as the system displays potentially impacted networks.

Other aspects are described below.

BRIEF DESCRIPTION OF DRAWINGS

At least one embodiment of the present invention will now be described with reference to the drawings and Table 2 at the end of the specification, in which.

DESCRIPTION OF EMBODIMENTS

Figure 1A:
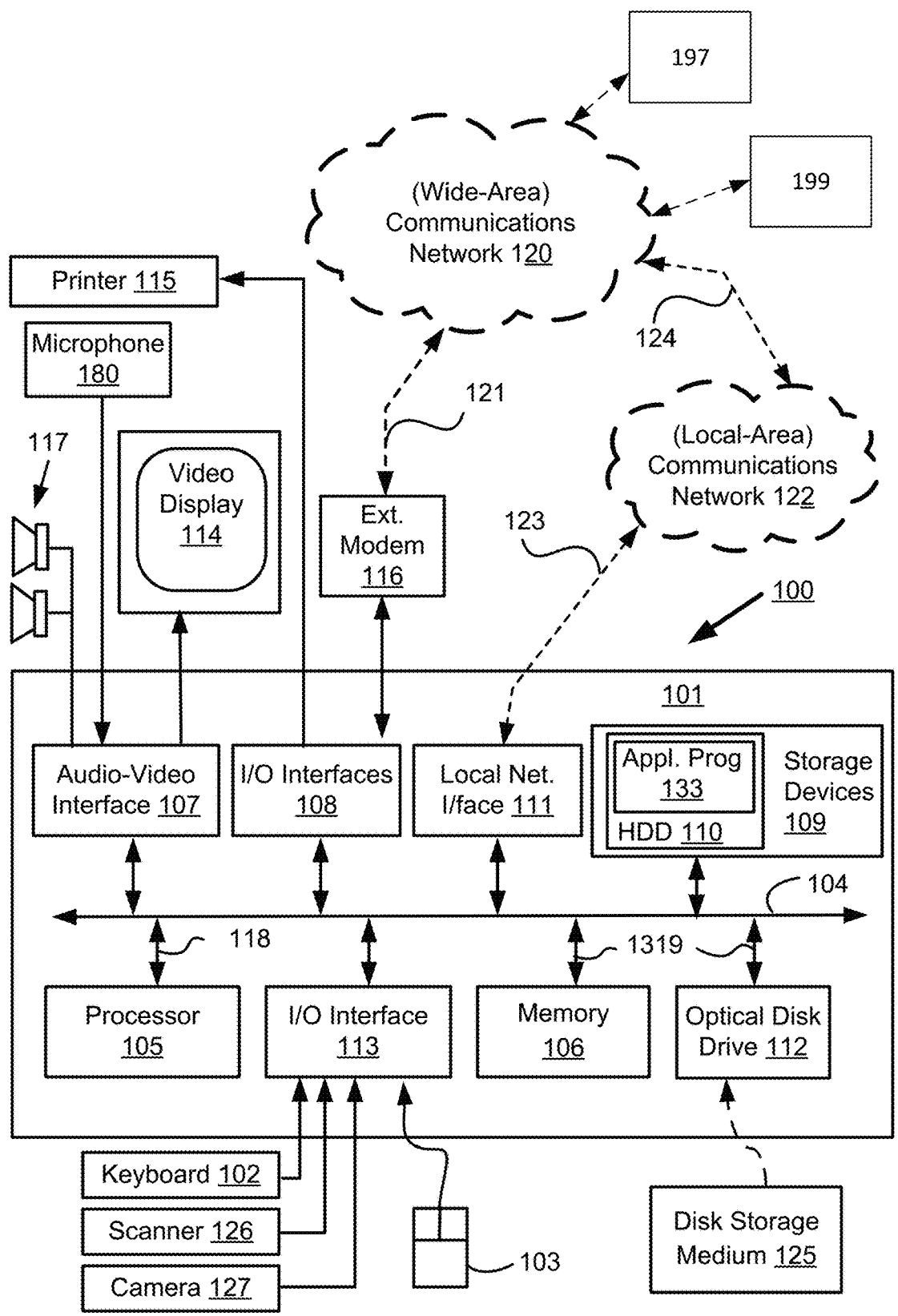
FIGS. 1A and 1B form a schematic block diagram of a computer system upon which arrangements described can be practiced.

Where reference is made in any one or more of the accompanying drawings to steps and/or features, which have the same reference numerals, those steps and/or features have for the purposes of this description the same function(s) or operation(s), unless the contrary intention appears.

A brain atlas is a method of representing portions of the human brain. A brain atlas typically comprises sections along anatomical or functional areas of a brain and provides a mapping of the brain. One can refer to the identified sections of the brain as parcellations of the brain. For example, one can delineate 180 areas/parcellations per hemisphere where the areas/parcellations are bounded by sharp changes in cortical architecture, function, connectivity, and/or topography. Such parcellations can be determined based on a precisely aligned group (e.g., more than 200) healthy young adults.

The arrangements described allow a user of a medical image display system, such as a neurosurgeon, to view DTI image data in a manner that just shows specified network(s) or interconnections of particular tracts and fibers corresponding to a particular function or structure of the brain. A graphical representation that identifies particular parcellations and corresponding tracts, or portions of tracts, relevant to the structure can be provided. A network of the brain can be constructed based upon parcellations of the brain and corresponding structural and functional connections.

The arrangements described allow use of DTI images for a subject to be provided in an improved manner so that a user can identify individual tracts or fibers relevant to interconnected or inter-operational portions of the brain. For example, tracts (or fibers) associated with particular parcellations or other known anatomical structures of the brain and the spatial relationships of the tracts (or fibers) with the parcellation can be represented graphically. Compared to previous solutions where all tracts in a region would be represented, thereby occluding relationships between tracts (or fibers) with one another and with certain portions of the brain, the user/viewer obtains a greater granularity in relation to the image data and a more clinically meaningful image. A neurosurgeon, for example, is thereby allowed an improved study of a subject brain, for example interconnections of particular tracts, regions, and networks. Given the more clinically meaningful image, the neurosurgeon can better understand connections and operations of the subject brain. Decisions relating to conditions, operation of the subject brain and procedures to be performed on the subject brain can be improved, thereby increasing patient safety and standard of care.

In order to allow a representation of the image data that isolates and identifies interconnections associated with a grouping, function or region of the brain, this specification provides a model mapping elements of the brain using atlas parcellations in accordance with a three-dimensional model of a brain. The model is effectively a library of neuroanatomy that can be used to assign parcellations of the brain into networks for particular function(s). Implementations of a system described in this specification can use the structure of the model to determine corresponding data from a DTI image and use that DTI data to graphically represent a particular network of the brain. Such a library structure further allows a user such as a neurosurgeon to use the graphical user interface accurately and intuitively to obtain a visual reconstruction of the brain of a particular subject to view network interconnections.

Figure 1B:
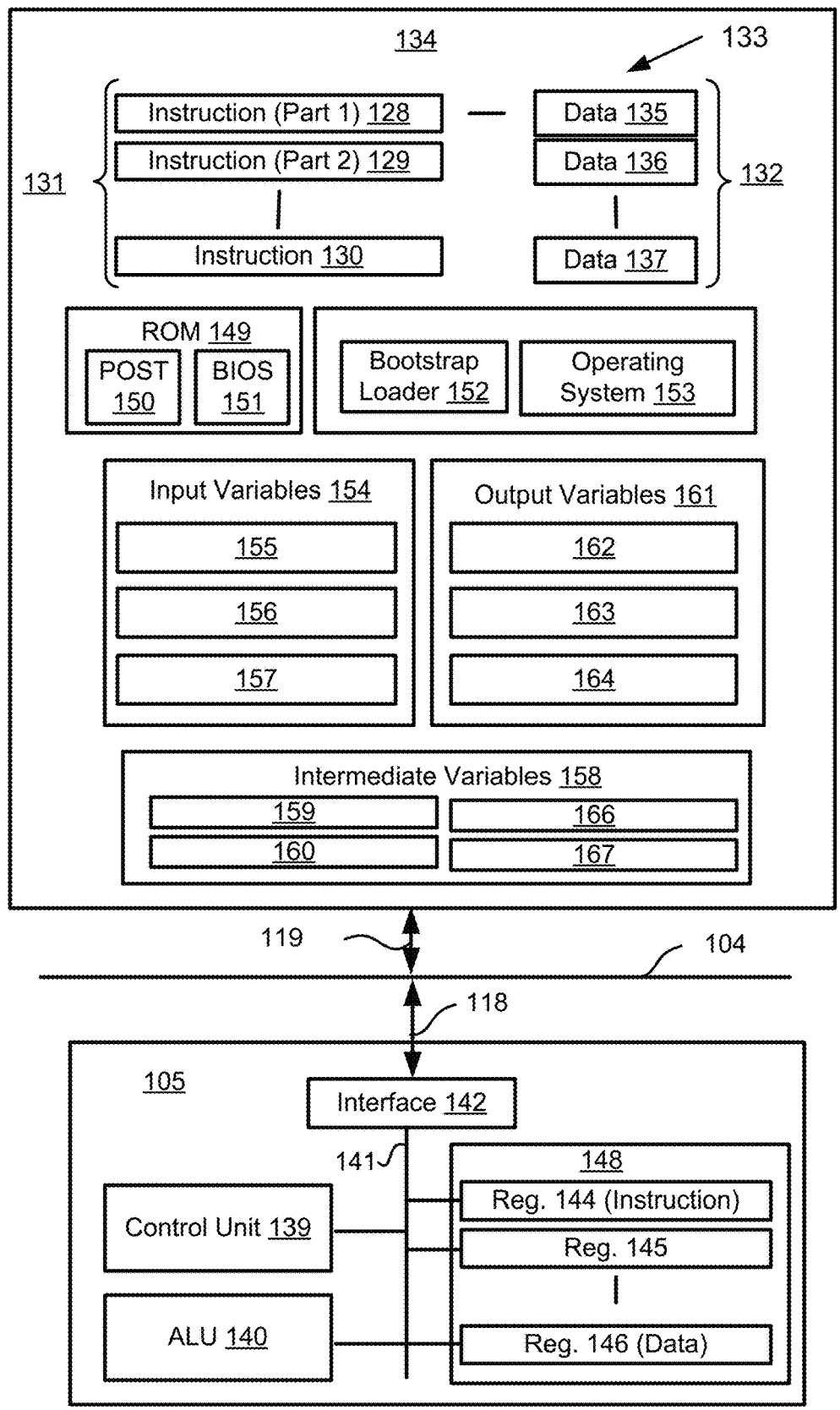

A computing device can perform the arrangements described. FIGS. 1A and 1B depict a computer system 100, upon which one can practice the various arrangements described.

As seen in FIG. 1A, the computer system 100 includes: a computer module 101; input devices such as a keyboard 102, a mouse pointer device 103, a scanner 126, a camera 127, and a microphone 180; and output devices including a printer 115, a display device 114 and loudspeakers 117. An external Modulator-Demodulator (Modem) transceiver device 116 may be used by the computer module 101 for communicating to and from a communications network 120 via a connection 121. The communications network 120 may be a wide-area network (WAN), such as the Internet, a cellular telecommunications network, or a private WAN. Where the connection 121 is a telephone line, the modem 116 may be a traditional "dial-up" modem. Alternatively, where the connection 121 is a high capacity (e.g., cable) connection, the modem 116 may be a broadband modem. A wireless modem may also be used for wireless connection to the communications network 120.

The computer module 101 typically includes at least one processor unit 105, and a memory unit 106. For example, the memory unit 106 may have semiconductor random access memory (RAM) and semiconductor read only memory (ROM). The computer module 101 also includes an number of input/output (I/O) interfaces including: an audio-video interface 107 that couples to the video display 114, loudspeakers 117 and microphone 180; an I/O interface 113 that couples to the keyboard 102, mouse 103, scanner 126, camera 127 and optionally a joystick or other human interface device (not illustrated); and an interface 108 for the external modem 116 and printer 115. In some implementations, the modem 116 may be incorporated within the computer module 101, for example within the interface 108. The computer module 101 also has a local network interface 111, which permits coupling of the computer system 100 via a connection 123 to a local-area communications network 122, known as a Local Area Network (LAN). As illustrated in FIG. 1A, the local communications network 122 may also couple to the wide network 120 via a connection 124, which would typically include a so-called "firewall" device or device of similar functionality. The local network interface 111 may comprise an Ethernet circuit card, a Bluetooth® wireless arrangement or an IEEE 802.11 wireless arrangement; however, numerous other types of interfaces may be practiced for the interface 111.

The module 101 can be connected with an image capture device 197 via the network 120. The device 197 can capture images of a subject brain using each of diffusor tension imaging and magnetic resonance imaging (MRI) techniques. The captured images are typically in standard formats such as DICOM format and OpenfMRI format respectively. The module 101 can receive DTI and MRI images the device 197 via the network 120. Alternatively, the DTI and MRI images can be received by the module 101 from a remote server, such as a cloud server 199, via the network 120. In other arrangements, the module 101 may be an integral part of one of the image capture device 197 and the server 199.

The I/O interfaces 108 and 113 may afford either or both of serial and parallel connectivity, the former typically being implemented according to the Universal Serial Bus (USB) standards and having corresponding USB connectors (not illustrated). Storage devices 109 are provided and typically include a hard disk drive (HDD) 110. Other storage devices such as a floppy disk drive and a magnetic tape drive (not illustrated) may also be used. An optical disk drive 112 is typically provided to act as a non-volatile source of data. Portable memory devices, such optical disks (e.g., CD-ROM, DVD, Blu ray Disc™), USB-RAM, portable, external hard drives, and floppy disks, for example, may be used as appropriate sources of data to the system 100.

The components 105 to 113 of the computer module 101 typically communicate via an interconnected bus 104 and in a manner that results in a conventional mode of operation of the computer system 100 known to those in the relevant art. For example, the processor 105 is coupled to the system bus 104 using a connection 118. Likewise, the memory 106 and optical disk drive 112 are coupled to the system bus 104 by connections 119. Examples of computers on which the described arrangements can be practised include IBM-PC's and compatibles, Sun Sparcstations, Apple Mac™ or like computer systems.

Figure 3:
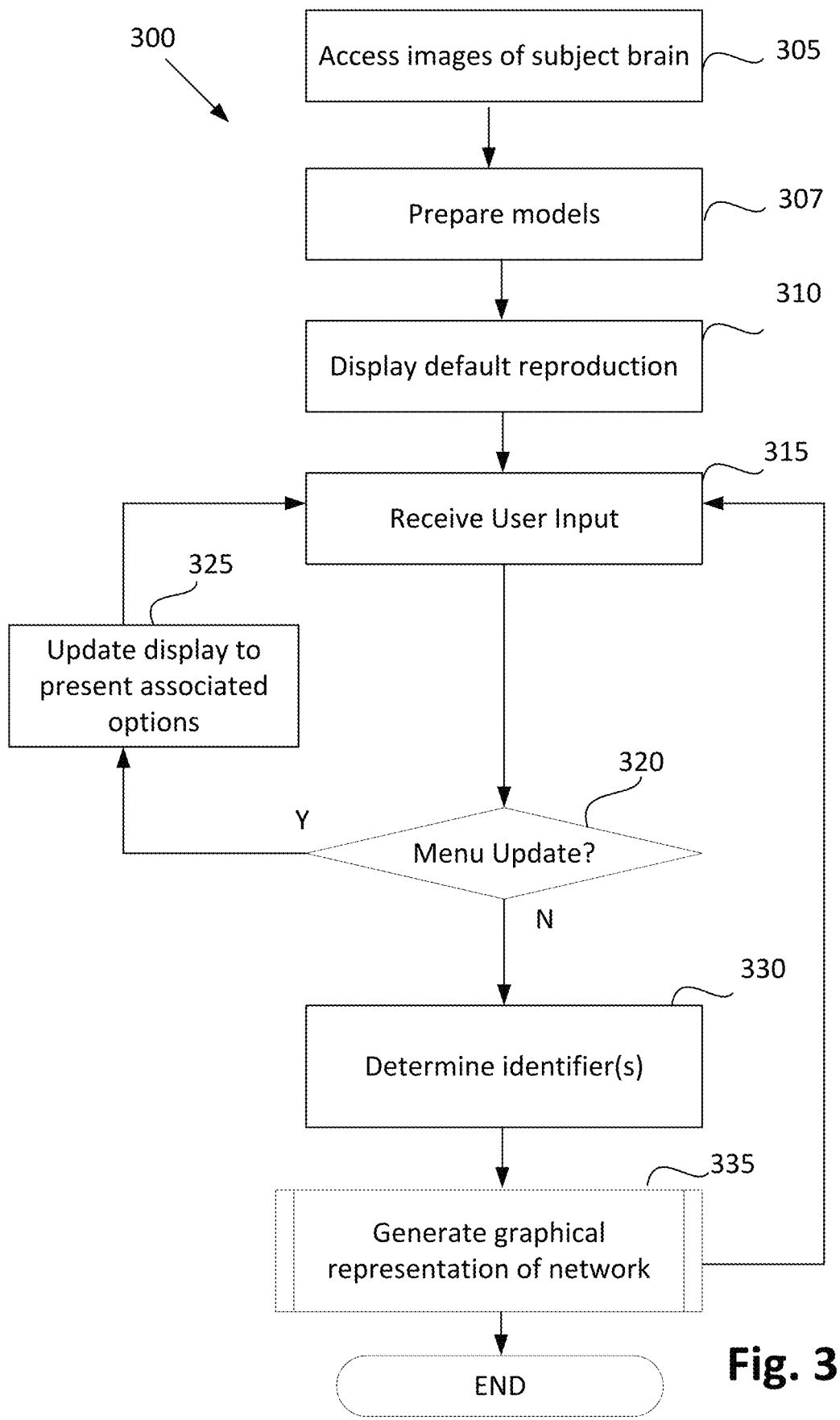
FIG. 3 shows a method of displaying a graphical representation of a network of a subject brain.
Figure 4:
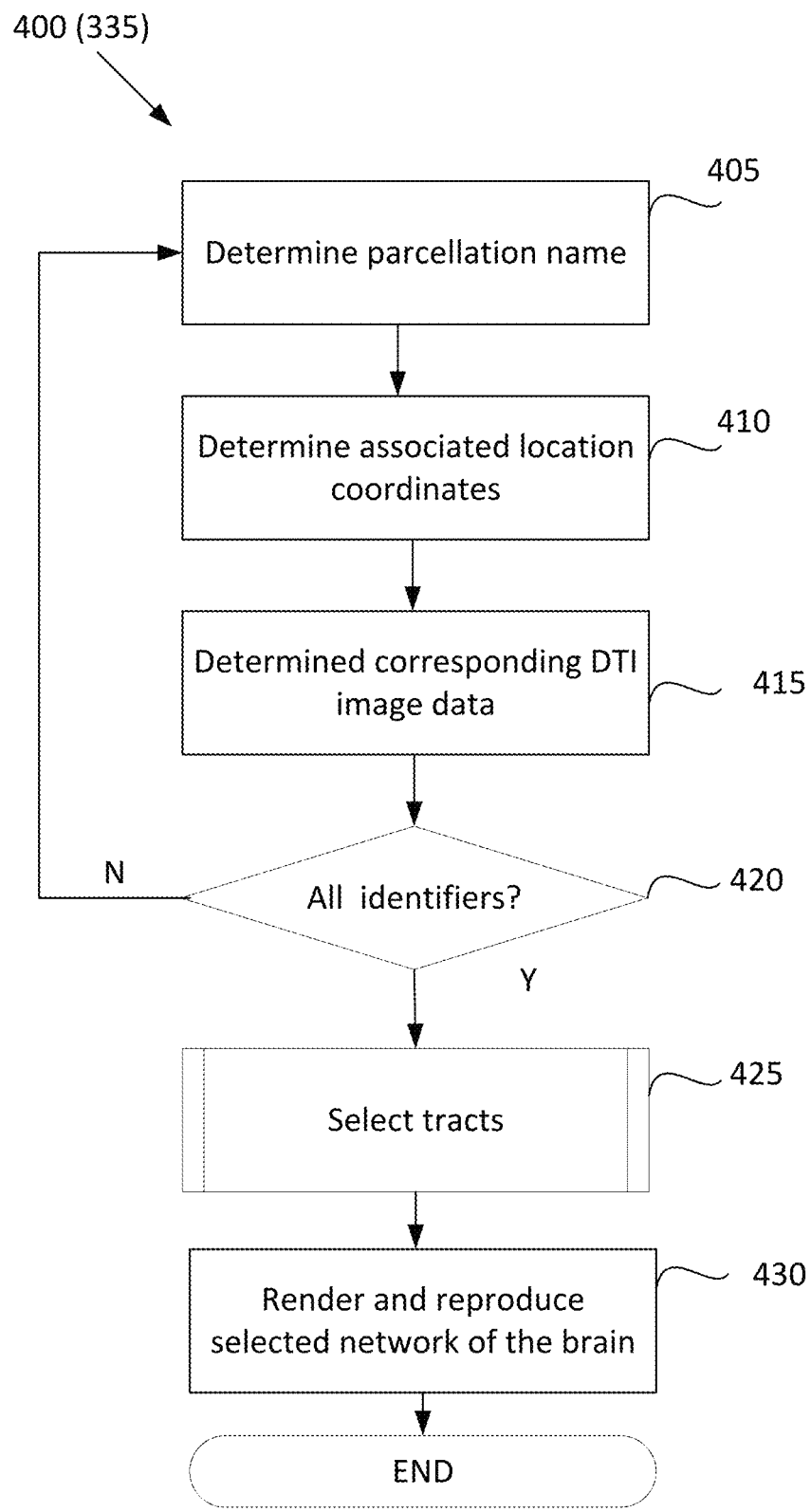
FIG. 4 shows a method of generating a graphical representation of a network of the subject brain as implemented in the method of FIG. 3.
Figure 5:
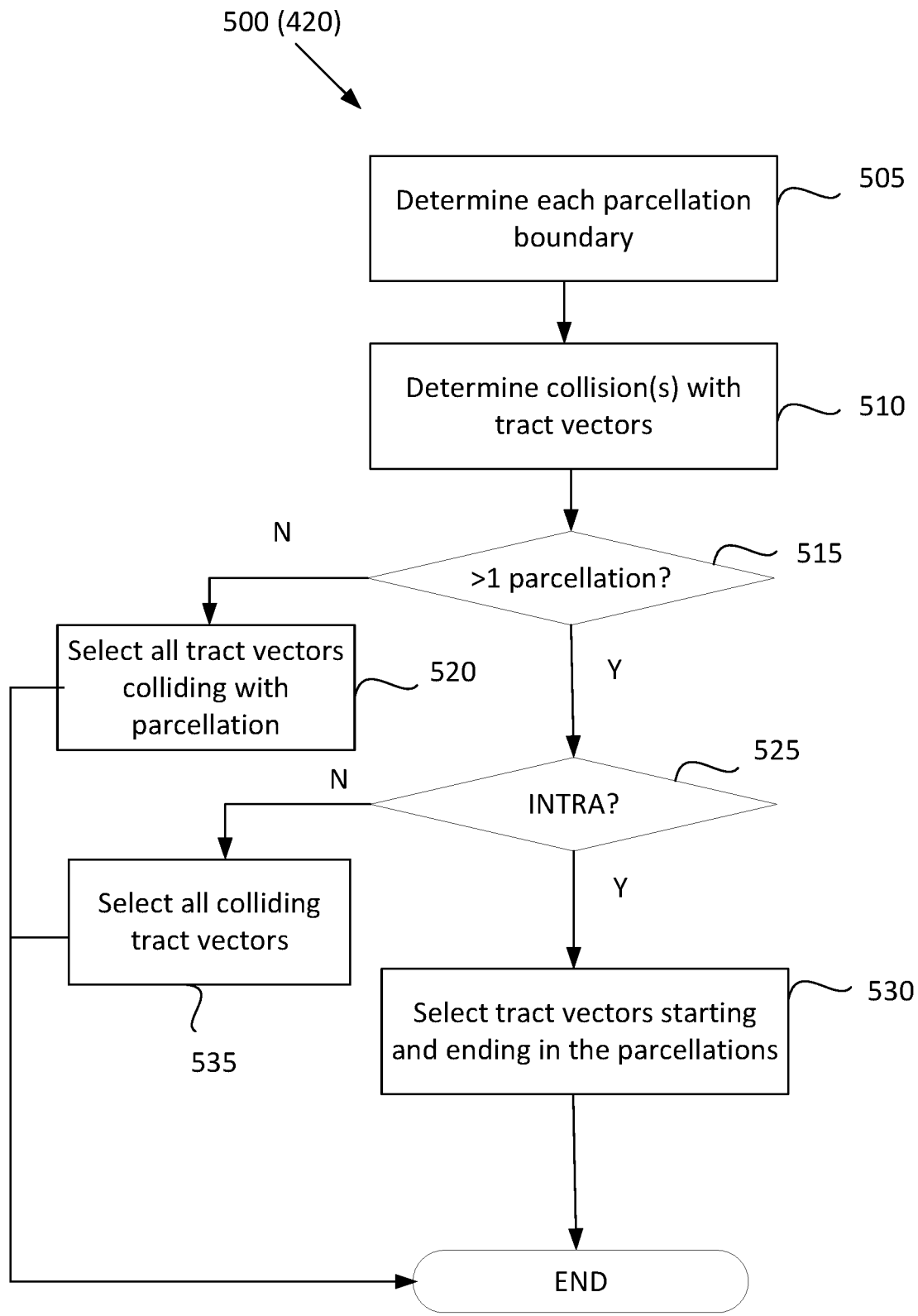
FIG. 5 shows method of identifying tracts as used in the method of FIG. 4.

The method described may be implemented using the computer system 100 wherein the processes of FIGS. 3 to 5, to be described, may be implemented as one or more software application programs 133 executable within the computer system 100. In particular, the steps of the method described are effected by instructions 131 (see FIG. 1B) in the software 133 that are carried out within the computer system 100. The software instructions 131 may be formed as one or more code modules, each for performing one or more particular tasks. The software may also be divided into two separate parts, in which a first part and the corresponding code modules performs the described methods and a second part and the corresponding code modules manage a user interface between the first part and the user.

The software may be stored in a computer readable medium, including the storage devices described below, for example. The software is loaded into the computer system 100 from the computer readable medium, and then executed by the computer system 100. A computer readable medium having such software or computer program recorded on the computer readable medium is a computer program product. The use of the computer program product in the computer system 100 preferably effects an advantageous apparatus for providing a display of a neurological image.

The software 133 is typically stored in the HDD 110 or the memory 106. The software is loaded into the computer system 100 from a computer readable medium, and executed by the computer system 100. Thus, for example, the software 133 may be stored on an optically readable disk storage medium (e.g., CD-ROM) 125 that is read by the optical disk drive 112. A computer readable medium having such software or computer program recorded on it is a computer program product. The use of the computer program product in the computer system 100 preferably effects an apparatus for providing a display of a neurological image.

In some instances, the application programs 133 may be supplied to the user encoded on one or more CD-ROMs 125 and read via the corresponding drive 112, or alternatively may be read by the user from the networks 120 or 122. Still further, the software can also be loaded into the computer system 100 from other computer readable media. Computer readable storage media refers to any non-transitory tangible storage medium that provides recorded instructions and/or data to the computer system 100 for execution and/or processing. Examples of such storage media include floppy disks, magnetic tape, CD-ROM, DVD, Blu-ray' Disc, a hard disk drive, a ROM or integrated circuit, USB memory, a magneto-optical disk, or a computer readable card such as a PCMCIA card and the like, whether or not such devices are internal or external of the computer module 101. Examples of transitory or non-tangible computer readable transmission media that may also participate in the provision of software, application programs, instructions and/or data to the computer module 101 include radio or infra-red transmission channels as well as a network connection to another computer or networked device, and the Internet or Intranets including e-mail transmissions and information recorded on Websites and the like.

The second part of the application programs 133 and the corresponding code modules mentioned above may be executed to implement one or more graphical user interfaces (GUIs) to be rendered or otherwise represented upon the display 114. Through manipulation of typically the keyboard 102 and the mouse 103, a user of the computer system 100 and the application may manipulate the interface in a functionally adaptable manner to provide controlling commands and/or input to the applications associated with the GUI(s). Other forms of functionally adaptable user interfaces may also be implemented, such as an audio interface utilizing speech prompts output via the loudspeakers 117 and user voice commands input via the microphone 180.

FIG. 1B is a detailed schematic block diagram of the processor 105 and a "memory" 134. The memory 134 represents a logical aggregation of all the memory modules (including the HDD 109 and semiconductor memory 106) that can be accessed by the computer module 101 in FIG. 1A.

When the computer module 101 is initially powered up, a power-on self-test (POST) program 150 executes. The POST program 150 is typically stored in a ROM 149 of the semiconductor memory 106 of FIG. 1A. A hardware device such as the ROM 149 storing software is sometimes referred to as firmware. The POST program 150 examines hardware within the computer module 101 to ensure proper functioning and typically checks the processor 105, the memory 134 (109, 106), and a basic input-output systems software (BIOS) module 151, also typically stored in the ROM 149, for correct operation. Once the POST program 150 has run successfully, the BIOS 151 activates the hard disk drive 110 of FIG. 1A. Activation of the hard disk drive 110 causes a bootstrap loader program 152 that is resident on the hard disk drive 110 to execute via the processor 105. This loads an operating system 153 into the RAM memory 106, upon which the operating system 153 commences operation. The operating system 153 is a system level application, executable by the processor 105, to fulfil various high level functions, including processor management, memory management, device management, storage management, software application interface, and generic user interface.

The operating system 153 manages the memory 134 (109, 106) to ensure that each process or application running on the computer module 101 has sufficient memory in which to execute without colliding with memory allocated to another process. Furthermore, the different types of memory available in the system 100 of FIG. 1A must be used properly so that each process can run effectively. Accordingly, the aggregated memory 134 is not intended to illustrate how particular segments of memory are allocated (unless otherwise stated), but rather to provide a general view of the memory accessible by the computer system 100 and how such is used.

As shown in FIG. 1B, the processor 105 includes a number of functional modules including a control unit 139, an arithmetic logic unit (ALU) 140, and a local or internal memory 148, sometimes called a cache memory. The cache memory 148 typically includes a number of storage registers 144-146 in a register section. One or more internal busses 141 functionally interconnect these functional modules. The processor 105 typically also has one or more interfaces 142 for communicating with external devices via the system bus 104, using a connection 118. The memory 134 is coupled to the bus 104 using a connection 119.

The application program 133 includes a sequence of instructions 131 that may include conditional branch and loop instructions. The program 133 may also include data 132 which is used in execution of the program 133. The instructions 131 and the data 132 are stored in memory locations 128, 129, 130 and 135, 136, 137, respectively.

Depending upon the relative size of the instructions 131 and the memory locations 128-130, a particular instruction may be stored in a single memory location as depicted by the instruction shown in the memory location 130. Alternately, an instruction may be segmented into a number of parts each of which is stored in a separate memory location, as depicted by the instruction segments shown in the memory locations 128 and 129.

In general, the processor 105 is given a set of instructions which are executed therein. The processor 105 waits for a subsequent input, to which the processor 105 reacts to by executing another set of instructions. Each input may be provided from one or more of a number of sources, including data generated by one or more of the input devices 102, 103, data received from an external source across one of the networks 120, 102, data retrieved from one of the storage devices 106, 109 or data retrieved from a storage medium 125 inserted into the corresponding reader 112, all depicted in FIG. 1A. The execution of a set of the instructions may in some cases result in output of data. Execution may also involve storing data or variables to the memory 134.

The described arrangements use input variables 154, which are stored in the memory 134 in corresponding memory locations 155, 156, 157. The described arrangements produce output variables 161, which are stored in the memory 134 in corresponding memory locations 162, 163, 164. Intermediate variables 158 may be stored in memory locations 159, 160, 166 and 167.

Referring to the processor 105 of FIG. 1B, the registers 144, 145, 146, the arithmetic logic unit (ALU) 140, and the control unit 139 work together to perform sequences of micro-operations needed to perform "fetch, decode, and execute" cycles for every instruction in the instruction set making up the program 133. Each fetch, decode, and execute cycle comprises:

a fetch operation, which fetches or reads an instruction 131 from a memory location 128, 129, 130;

a decode operation in which the control unit 139 determines which instruction has been fetched; and an execute operation in which the control unit 139 and/or the ALU 140 execute the instruction.

Thereafter, a further fetch, decode, and execute cycle for the next instruction may be executed. Similarly, a store cycle may be performed by which the control unit 139 stores or writes a value to a memory location 132.

Each step or sub-process in the processes of FIGS. 3 to 5 is associated with one or more segments of the program 133 and is performed by the register section 144, 145, 147, the ALU 140, and the control unit 139 in the processor 105 working together to perform the fetch, decode, and execute cycles for every instruction in the instruction set for the noted segments of the program 133.

FIG. 2 shows a software architecture 200 for implementing a graphical user interface to reconstruct and display a network of a subject brain. The architecture 200 includes a surface mesh 202, a mesh model 204, a mapping database 206 and an interface module 210, each of which is typically stored in the memory 106. The interface engine 210 typically forms one of the modules of the software application 133 executable on the processor 105. A mesh is a term often used in 3D computer rendering to describe a file that contains a cloud of points in space or a formula the rendering of which will create that cloud. In the present case, a mesh can provide the coordinates at which the parcellations are drawn. There can exist two meshes, a surface mesh and a mesh model. The surface mesh 202 can provide the color to display for each relevant parcellation and the mesh model 204 can provide the voxel identity for use with the database of parcellations. Note that this is just one possible implementation of the rendering method.

The interface module 210 executes to generate or render a graphical user interface displayed on the monitor 114 for example. The graphical user interface includes a number of menu options and a graphical representation of a network of a brain or a captured image of the brain. The interface model typically forms one or more modules of the application 133. In some arrangements, the module 210 may be accessed or distributed by an internet browser executing on the module 101.

The mesh model 204 represents a three-dimensional structure of a shape of a brain of a subject. The mesh model 204 can be constructed using a point-cloud or a mesh of three-dimensional objects such as voxels. In the example arrangements described herein, the mesh model comprises cubic objects each representing a voxel. Each of the cubic objects has an associated location in three-dimensional space (x, y and z coordinates) representing the brain. Each point or voxel in the mesh model 204 has an associated mesh identifier.

The surface mesh 202 comprises a model of the subject brain in which color (described as a set of RGB values) is applied to voxels to generate a surface representing parcellations of the brain. Voxels can be assigned to parcellations using one of a variety of methods. In other words, the mesh can be derived from a personalised atlas in one implementation. In other implementations, other atlases can be used. For instance, one can use a warped HCP with no correction using a machine learning model. The parcellations represent regions of the brain. The RGB values are preferably assigned to parcellations in the following manner. The mesh is a cloud of points in space. Those points have an RGB value that can be derived from a look up table. The surface model 202 associates a set of RGB values with a coordinate of each voxel, the RGB values reflecting a parcellation of the subject brain. Alternatively, other methods of assigning color may be used. Both of the surface mesh 202 and the mesh model 204 are generated for each subject brain. The surface mesh 202 and the mesh model 204 are generated using MRI data for the image brain as described in relation to FIG. 3 below. A color scheme is not required as parcellations involved in homogeneous functions are displayed in shades of the same color. Using such a color scheme makes the display easier for a user to digest.

The mapping database 206 stores the model or library used to classify portions of the brain into parcellations. The parcellations relate to a brain atlas and can be assigned identifiers in a specific order, as described in more detail hereafter. The structure of the mapping database 206 allows the user to select required parcellations or networks of the brain for which a network is to be generated using a graphical user interface.

The interface module 210 executes to use the surface mesh 202, mesh model 204, the mapping database 206, and image data (both DTI and MRI) to render and display or reproduce a graphical representation of a network of the brain based on a user selection.

Figure 2A:
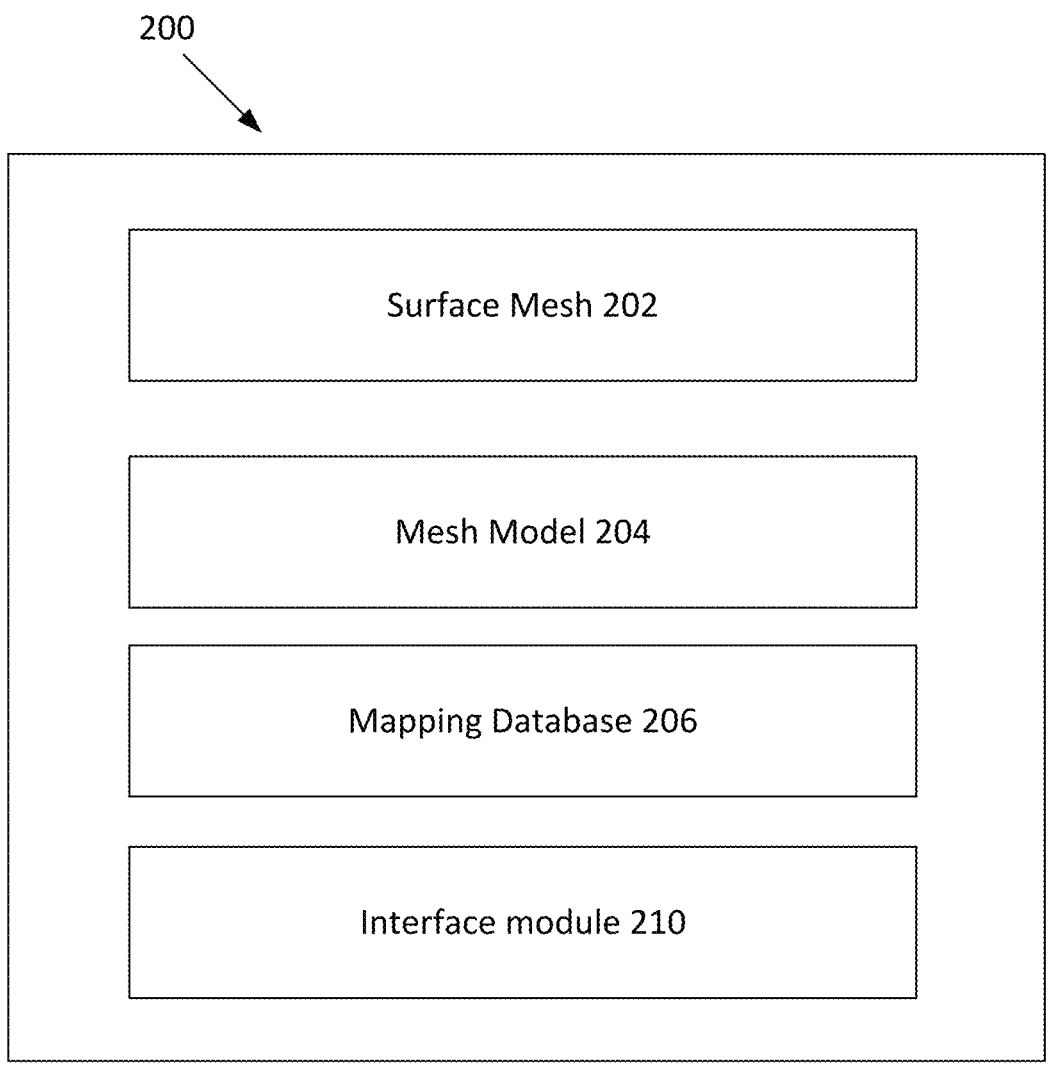
FIG. 2A shows a software architecture for a graphical user interface for reproducing a graphical representation of specified network(s) of a brain.
Figure 2B:
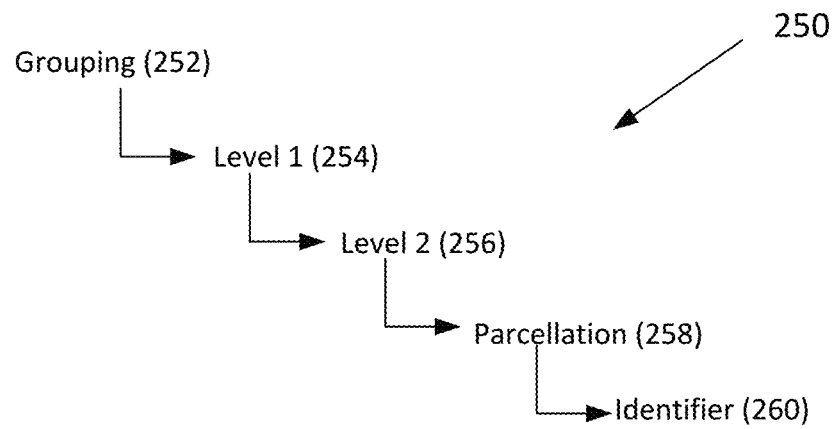
FIG. 2B shows a data structure used in a database of FIG. 2A.

FIG. 2B shows one example of a data structure of the mapping database 206. As shown in FIG. 2B a data structure 250 has a highest level 252 named "Grouping". The Grouping represents an initial menu option into which a user can drill down, if desired, to identify a particular network of the brain to be represented graphically. A next level of the structure 250 after the Grouping is termed Level 1 marked as 254, followed by Level 2 (marked as 256), in turn followed by a Parcellation Level marked as 258. The Parcellation Level 258 is also referred to as a parcellation name. Each Parcellation Level 258 is associated with a unique identifier 260, referred to as a parcellation identifier. As described in relation to FIG. 4 below, each parcellation name 258 is determined based on the mapping database 206 connecting three-dimensional locations in the subject brain with a parcellation identifier 260. Another implementation of the data structure of the mapping database 206 can have more or fewer levels.

An example of a mapping database 206 providing a library of a brain using the data structure 250 is shown in Table 2 at the end of the specification. As shown in Table 2, a particular sub-level may not be present for some of the levels 252 and 254.

Table 1 below shows an example set of Grouping options.

TABLE 1

| Grouping options |
| Grouping Types |
| --- |
| Network |
| Parcellation |
| Tract |
| Region |

The naming of grouping types can take various forms. For example, instead of a "Network" grouping type one can have a "Network template" grouping type and/or instead of a "Tracts" grouping type, one can have a "Tractography Bundle" grouping type.

In the context of the arrangements described a graphical representation of a network of a brain relates to parcellations of the brain and/or associated tracts. The graphical representation of the network of the brain can relate to selection of any of the Groupings "Network", "Parcellation", "Tract" and "Region" and associated sub-levels.

Figure 7A:
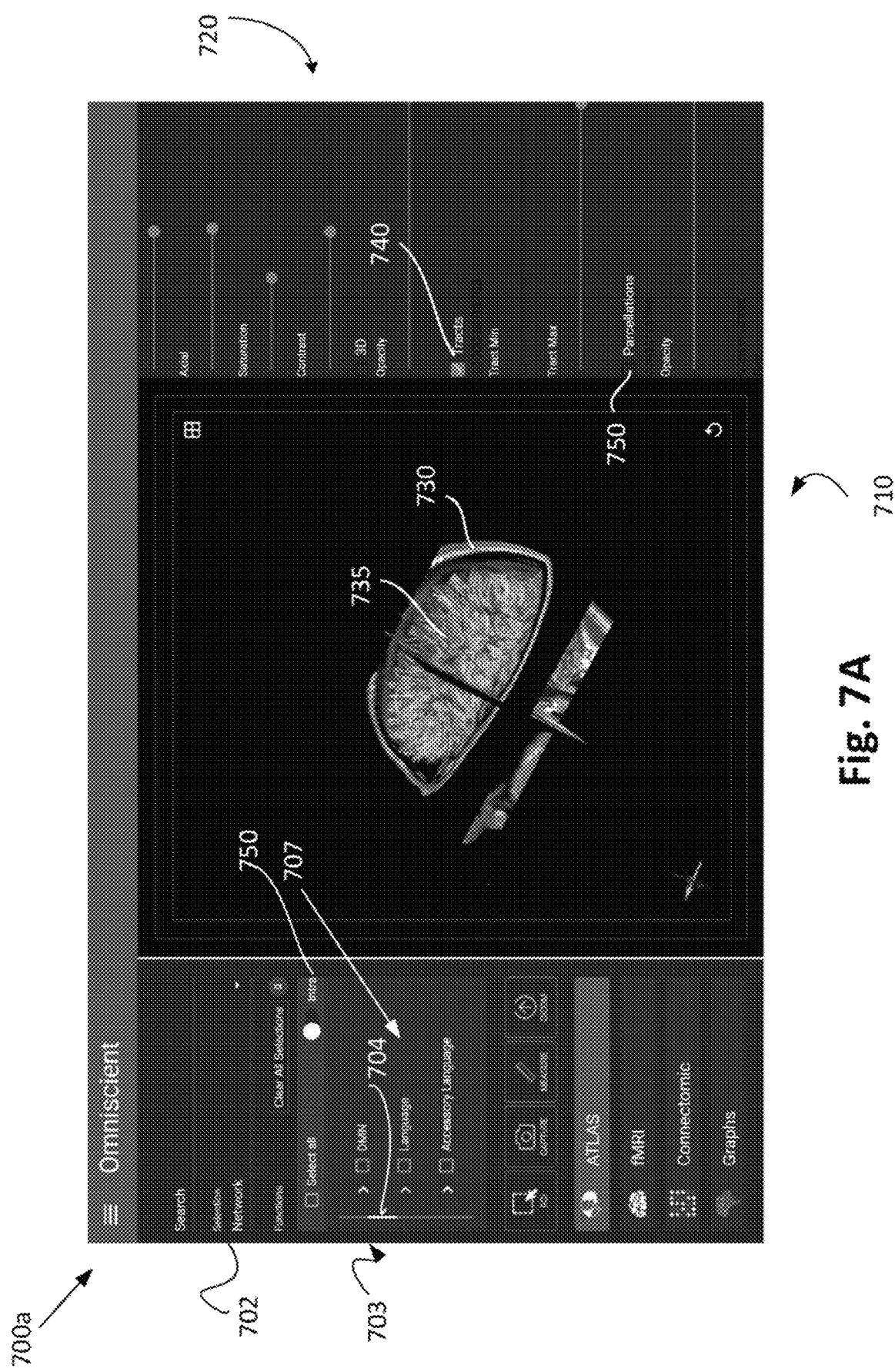
FIG. 7A shows a window of a graphical user interface showing image data of a subject brain.

FIG. 7A shows an example of a window 700a rendered by execution of the interface module 210 on the module 101. The window 700a can be reproduced via the display 114 for example. The window 700a includes a pull-down menu 702. The options available in the pull-down menu 702 reflect the Grouping options of Table 1 (Grouping 252 of the data structure 250).

Each of the levels 254 and 256 represent a portion of the brain, sub-divided in a progression such that the parcellation level (name) 258 represents a typical parcellation of the brain used in a brain atlas. The representations provided by the levels 254 and 256 depend on the corresponding Grouping 252. For example, in Table 2 below some Groupings have a left Level 1 category and a right level 1 category for each of left and right. As shown in Table 2, the same parcellation name 258 can be applied to more than one identifier as a parcellation may be relevant to more than one location or region (for example parcellation name "8C" is applied to identifiers 73 and 273 relating to left and right instances of Level 1 (auditory function) respectively). One can design the structure 250 to divide portions of the brain in a manner intuitive to a neurosurgeon or another neuroscience professional. One can use the data structure 250 to identify relevant areas of a subject brain and/or of a DTI image as described below.

Referring to FIG. 7A, the window 700a includes a sub-menu 703 with a slider 704. The sub-menu 703 includes options 707 reflecting Level 1 (254) associated with the Grouping "Network". Each of the options reflecting Level 1 can be selected by a user or expanded into Level 2 (256) if available or the next sub-level until the Parcellation Level 258 is reached.

The Grouping "Network" can relate to a network based on particular function such as auditory or language. The data structure 250 can be generated to reflect known scientific classifications of the human brain. The data structure 250 allows actual structure and/or function of the human brain to be programmatically extracted so that different portions of a subject brain and their interconnects can be identified and represented graphically. In particular, breaking the Grouping 252 into different levels that lead to parcellations allows structure and/or function to be extracted, e.g., on the basis of specified network(s).

The structure 250 shown in FIG. 2B and the example database shown in Table 2 reflect anatomical breakdown in a manner intuitive to typical neurosurgeons to form a preferred implementation. However, the structure 250 can be varied in other implementations, for example adding further levels, merging the levels 254 and 256, or otherwise further subdividing the Grouping 252.

The mapping database 206 and the mesh model 204 operate to associate the parcellation identifier 260 with a three-dimensional coordinate ((x, y, z) coordinates) in the subject brain. A relationship is established between the mesh identifiers of the mesh model 204 and the parcellation identifiers 260. For example, each point or voxel of the mesh model 204 can be associated with one of a sequential number of mesh identifiers representing a rasterization of three-dimensional locations in the brain. The mapping database 206 associates the parcellation identifier 260 with the parcellation name 258 as shown in FIG. 2B. Accordingly, the parcellation name 258 can be in turn associated with three-dimensional coordinates in the three-dimensional mesh model. Additionally, RGB values, each having values of between 0 and 255 are associated with each parcellation name and/or identifier using the same coordinate system. An example is shown in Table 2 where the mesh identifier is associated with the parcellation.

two-dimensional models and coordinates. For example, in some circumstances a neurosurgeon may prefer to use a two-dimensional model for improved ease of perception and reference, whereas in other circumstances (for example during surgery) three-dimensional model may be more appropriate.

FIG. 3 shows a method 300 of displaying a graphical representation of a network of a brain. With reference to FIGS. 1A, 2A and 3, the method 300 is executed by the interface engine 210 under execution of the processor 105.

The method 300 starts at an accessing step 305. At step 305 a system (such as the system illustrated in FIG. 1A) accesses images of a subject brain. The images are DTI and MRI images captured of the same subject brain, for example the image capture device 197 can capture the images and transmit them to the module 101 via the network 120 or the images may be already stored in memory 106.

The method 300 continues from step 305 to a model preparation step 307. The step 307 operates to use the accessed MRI image data to construct a greyscale brain image, the mesh model 204, and the surface mesh 202 and populate the mapping database 206 for the subject brain.

T1 data of the MRI image allows construction of a greyscale brain image according to known techniques. The T1 data represents a three-dimensional model of the subject brain in which each voxel is associated with a greyscale value.

The step 307 operates to generate the mesh model 204 based on the voxel positions. Each voxel or point in the mesh model has a three-dimensional location in the image. The step 307 executes to assign a mesh identifier to each of the voxels. For example, the identifier can be based on a rasterization of the T1 data of the MRI image.

Population of the database structure 206 is achieved by associating voxels of the three-dimensional image of the subject brain (available via T1 data of the MRI) with one of the parcellation identifiers 260. Each parcellation identifier 260 is assigned in a specific order to establish a relationship with the mesh identifiers. In the arrangements described

TABLE 2

| Mapping database and mesh relationships | | | | | |
|---|---|---|---|---|---|
| Mesh Identifier MID (stored in 204) | Mesh Coordinate (x, y, z) (Stored in 204) | Parcellation Identifer MID (stored in 206) | Parcellation name (stored in 206) | Color (R, G, B) (stored in 206) | Surface mesh 202 (MID with RGB applied to voxel) |

In one implementation, the data included in the surface mesh, the mesh model and the mapping database can be as follows: 1) surface mesh—Mesh coordinate, mesh ID, color, parcellation name, voxel ID; 2) mesh model—mesh ID, mesh coordinate, parcellation ID; and 3) mapping database—grouping, level 1, level 2, parcellation name, parcellation ID. In a specific implementation, Table 2 reflects the mapping database. The mesh gives the parcellation id in space that the rendering engine can interpret. Putting the mapping database and the mesh model together one can obtain the surface mesh, i.e., parcellations colored in space. With a different file system, the surface mesh and the mesh model can be collapsed in one object. The example arrangements described relate to use of three-dimensional models and coordinates. However, in instances where a two-dimensional representation of portions of a brain may be required, the implementation described can be applied similarly to use each parcellation identifier 260 in the database is assigned based on values as the mesh identifier in the corresponding (same) location in the mesh model 204. In other words, a particular parcellation identifier can be assigned to various mesh identifiers in such a way as to use sequential mesh identifiers for voxels belonging to a single parcellation. This approach leverages the principle of database normalisation where normal forms are stored separately to avoid redundancy and easy update. If the system stores coordinates and colors in the same database, one would have to update the whole database as soon as one updates the coordinates (e.g., for a new brain). Similarly if one updates the colors one would have to update all the scans processed to date. Stated differently, ID's are invariants that are used to look up elements that can change. In other arrangements, the parcellation identifier and the mesh identifier may be associated using other methods such as an algorithm or a look up table.

The mesh surface 202 and the mesh model 204 allow a parcellation name 258 to be matched to a volume in space and the identifiers 260 to be populated.

The surface model 202 is also generated at step 307 based on voxel positions determined from the MRI data. Each of the voxels is associated with a set of RGB values in the database 206 for the corresponding parcellation value. The RGB values can be stored as part of the mapping database 206 or the surface mesh 202. The RGB values can be derived as described above The association of the coordinates of the mesh and the parcellations, and thereby the RGB values are based upon a brain atlas. For example, a standard HCP-MMP atlas, after conversion to a volumetric format such as NIFTI, can be loaded and fitted to the T1 data of the subject brain using fitting mechanisms such as curve fitting techniques, least squares fitting techniques, or volumetric fitting.

With reference to FIG. 3, the method 300 continues from step 307 to a displaying step 310. With reference to FIGS. 1A and 3, the step 310 operates to reproduce a default display of the graphical user interface, for example in the monitor 114. The default reproduction can be the window 700a of FIG. 7A, for example. The window 700a includes an area 710 in which a graphical representation of a brain, or a network of a brain, can be reproduced. In the example of FIG. 7A, a default representation is reproduced, being DTI image data for the full subject brain superimposed over the greyscale T1 image. In the example of FIG. 7A, 730 shows greyscale graphics relating to the MRI data and 735 shows graphics relating to the tracts determined from the DTI image.

The window generated by the interface can include a set of sliders 720 for adjusting graphical elements of the interface display such as contrast. The user can manipulate inputs of the module 101 such as the mouse 103 to adjust the sliders 720. The menu 720 also includes options relating to display of tracts and parcellations. In the example of FIG. 7A, check-boxes 740 and 750 allow display of tracts and parcellations to be switched on or off respectively. In the example of FIG. 7A, tracts are turned on (740 checked) and parcellations are turned off (750 unchecked).

Figure 11:
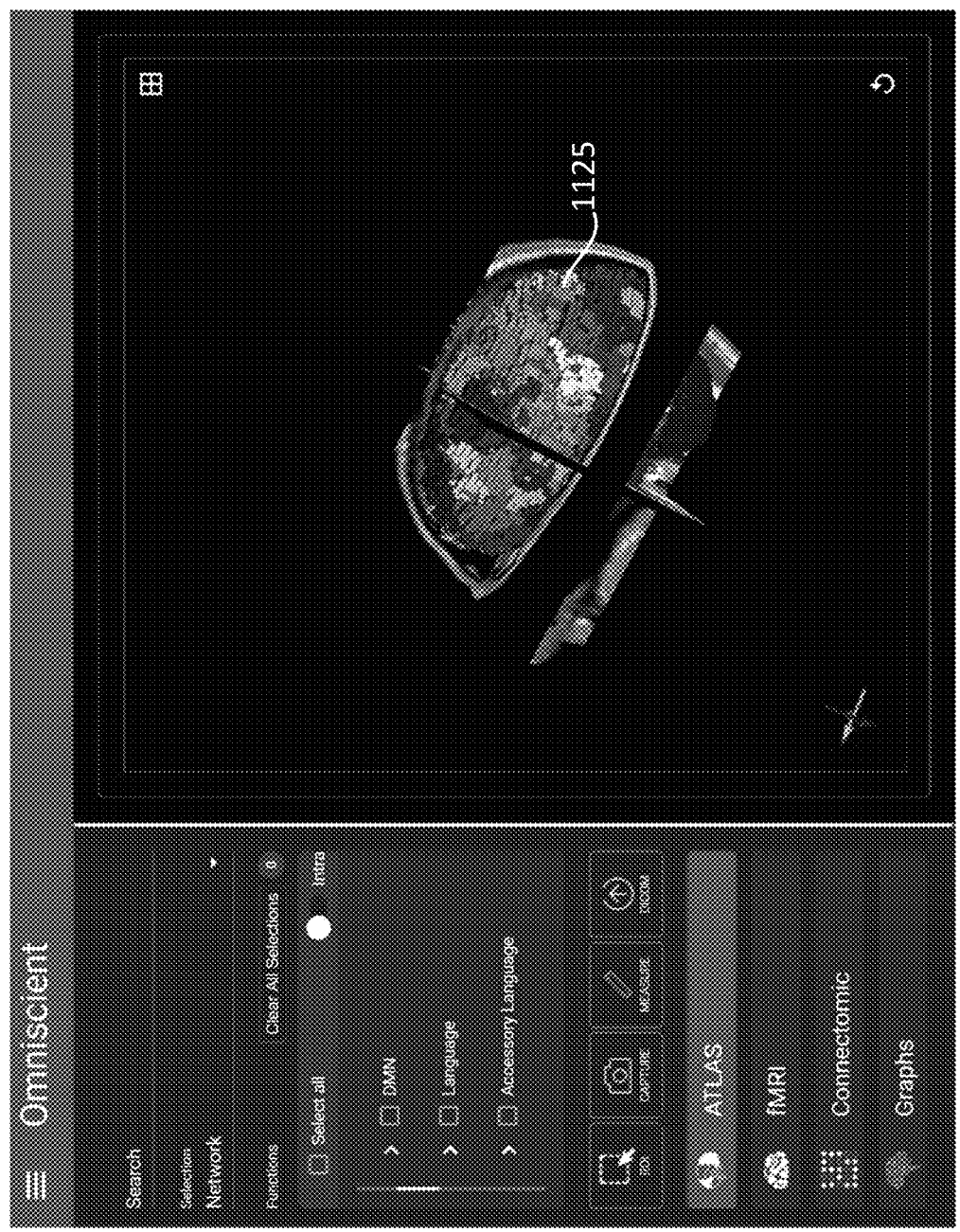
FIG. 11 shows another window of a graphical user interface showing a graphical representation of a network of a brain; and Table 2 at the end of the specification shows a mapping database using the structure of FIG. 2B.

In another implementation, the default display can relate to the surface mesh 202. FIG. 11 shows a window 1100 reproduced by execution of the interface module 210. The window 1100 shows an example default display in which only parcellation surfaces 1125 are reproduced rather than the tracts described by the DTI image. The window 1100 relates to the check-box 740 being unchecked and the check-box 750 being checked (see FIG. 7A).

Returning to FIG. 3, the method 300 continues from step 310 to a receiving step 315. The step 315 operates to receive a user input. The input is received due to a user manipulating an input of the module 101, for example the mouse 103, to interact with the graphical user interface, for example the window 700.

On receiving the input at step 315 the method 300 continues under control of the processor 105 to a check step 320. Step 320 executes to check if the interaction requires a menu update. A menu update may be required if the user has selected a different option from the menu 703 of FIG. 7A, or selects to expand a currently available menu option, for example one of options 707 available next to the slider 704. The options 707 represent options corresponding to Level 1 (254) of the data structure 250, each of which can be selected by the user or expended. Each of the options at Level 1 can be selected or expanded to provide a sub-menu corresponding to Level 2 (256) The Level 2 options can in turn be selected or expanded to represent selectable sub-options representing corresponding parcellation levels or names (258).

Figure 8:
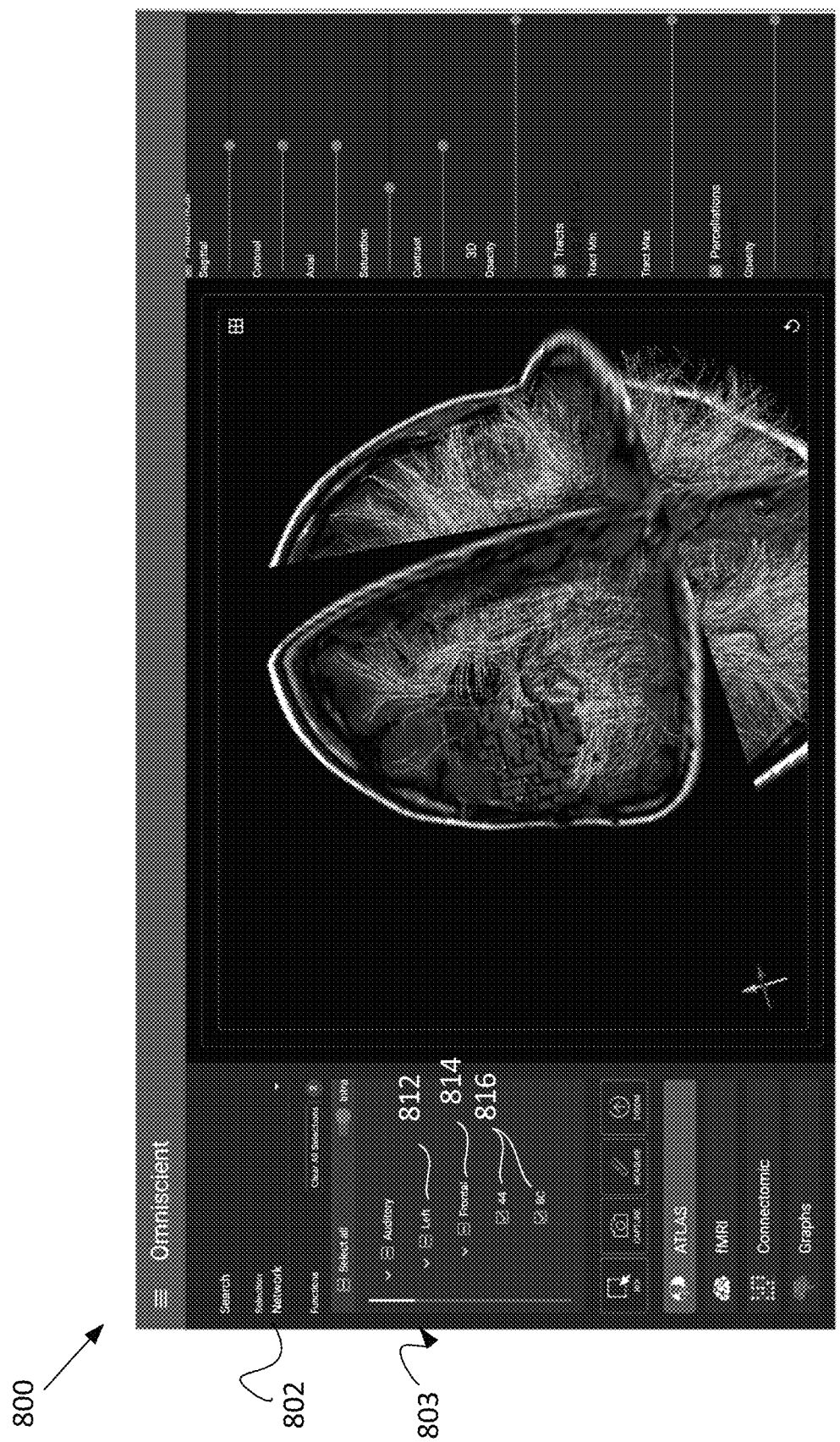
FIG. 8 shows a window of a graphical user interface showing image data of a subject brain and an updated menu.

If step 320 determines that a menu update is required ("Y" at step 320), the method 300 continues to an updating step 325. The updating step updates the graphical user interface to display menu options available as a result of the interaction. For example, FIG. 8 shows a window 800 reproduced by the interface engine 210. A pull-down menu 802 (corresponding to the menu 702) shows a Grouping selection of "Network". In the window 800 a menu area 803 (similar to the area 703) has had Level 1 (254) and a corresponding instance of Level 2 (256) expanded. In the window 800 Level 1, Level 2 and Parcellation Level 258 options are displayed as 812, 814 and 816 respectively.

Returning to FIG. 3, if step 320 determines that a menu update is not required ("N" at step 320), the method 300 continues to a determining step 330. The step 330 is therefore executed if the user has made a selection that requires a network of a brain to be graphically represented. The step 330 operates to determine each parcellation identifier (260) associated with the user selection. Step 330 can execute to determine more than one parcellation identifier, depending on the user selection. For example, the user has selected more than one parcellation 258, each parcellation has an associated identifier 260. Alternatively, if the user has selected a Level 1 (254) or Level 2 (256) option, the network can contain more than one parcellation such that more than one parcellation identifier is inherently selected. For example, with reference to FIG. 7A if the user selects the "language" option from the options 707, the system selects all the pacellations that are part of the language function.

The method 300 continues under execution of the processor 105 from step 330 to a generating step 335. The step 335 executes to generate a graphical representation of the selected network of the subject brain. Step 335 uses the parcellation identifiers (260) determined in step 330, the mesh model 204 and the surface mesh 202 generated at step 307, and the image data accessed at step 305 to generate a graphical representation of the network of the subject brain selected by the user. Operation of step 335 is described in greater detail in relation to FIG. 4.

FIG. 4 shows an example of a method 400 of generating a graphical representation of a brain as executed at step 335. The method 400 is typically implemented as one or more modules of the application 210 stored in the memory 106 and controlled under execution of the processor 105.

The method 400 receives the parcellation identifiers 260 determined at step 330. The step 405 operates to select one of the received parcellation identifiers. The selection may be based on any suitable criteria, for example location, numerical order or random. A parcellation name 258 corresponding to the selected identifier is determined at step 405 using the mapping database 206. Linking the selection menu to the rendering uses ID's. For example, a user can select a network name using a user interface. The system uses the network name to identify parcellation IDs and the system uses the parcellation IDs to determine where the parcellations are in 3D space. Steps 330 and 405 operate to determine, based on the MRI image of the subject brain and the identifiers associated with the user selection, one or more parcellations of the subject brain.

The method 400 continues under control of the processor 105 from step 405 to a determining step 410. Step 410 operates to determine three-dimensional coordinates for the parcellation name 258. The three-dimensional coordinates reflect a location or region in three-dimensional space on the mesh model 204. The three-dimensional coordinates are determined by matching the parcellation name 258 and/or the associated identifier(s) 260 with identifiers of the mesh model 204. The coordinates are those of the matched mesh identifiers. In implementations where the data structure 250 is varied, identifiers from different levels may be used. In other words, the left hand side menu can show different subsets such as "Networks" or "tracts." An implementation of the system enables updates over the parcellation database. As a result, the left hand side menu can be updated. Since the system can use ID's, the matching with the mesh is preserved.

The method 400 continues from step 410 to a determining step 415. The step 415 operates to determine image data corresponding to the location or region identified at step 410 from the DTI image accessed at step 305. The DTI image data is typically in ".TRK" format in which tracts are represented as lists of tract vectors having three-dimensional locations. The system can identify tract vectors corresponding to the location or region determined at step 410. In one arrangement, the coordinates associated with the three-dimensional mesh model 204 have a same origin as the image data such that the same three-dimensional location can be used for each. In other arrangements, a translation of vectors may be required to align origins of the image data and the mesh model 204. Step 415 effectively determines all tracts relevant to the user selection.

The method 400 continues from step 415 to a check step 420. As noted in relation to step 330 the user's selection can result in more than one identifier being determined. Step 420 executes to check if image data has been determined for all of the identifiers received as inputs to the method 400. If image data has been determined for all received identifiers ("Y" at step 420) the method 400 continues to an identifying step 425. If image data has not been determined for all received identifiers ("N" at step 420) a next identifier is selected and the method 400 returns to step 405. The system then repeats steps 405 to 415 for the next selected identifier.

The step 425 executes to select tracts from the image data that are relevant to the network indicated by the user input, effectively organising the tracts determined in each iteration of step 415 into subsets based on the user selection. The tracts can relate to full tracts or subsets of tracts. The subsets of tracts can include individual fibers. The tract vectors comprise sequences of vectors present in the image data that in combination represent routing of tracts. The system selects the tracts based on intersection (also referred to as collision) with one or more volumes bounded by the selected parcellations. The volumes are determined based on the coordinates determined at step 410. Steps 415 and 425 relate to determining corresponding tracts in a diffusion tensor image of the brain. The determination is made using the coordinates determined at step 410. Operation of the step 425 is described in further detail in relation to FIG. 5.

The method 400 continues from step 425 to a rendering step 430. At step 430 the interface module 210 executes to render a graphical representation of the brain network and reproduce the graphical display for the user (for example via the video display 114). The graphical representation includes at least one of (i) one or more surfaces, each representing a parcellation boundary, and (ii) the tracts selected at step 425. The graphical representation can include a greyscale image providing a background reference. Whether the graphical representation relates to both the parcellation surfaces and the selected tracts or just one of the selected tracts and the parcellation surfaces alone depends on the selection received from the user at step 315.

Step 430 operates to generate surfaces representing parcellation boundaries (if required) based on the coordinates determined at step 410 and the RGB values of the database 206 associated with the corresponding parcellation name. Each required surface is generated using selection of the regions defined in the surface mesh 202. If the user selection requires the tracts to be included in the graphical representation, the tract vectors of the DT image are used to generate the corresponding graphical representation.

Figure 7B:
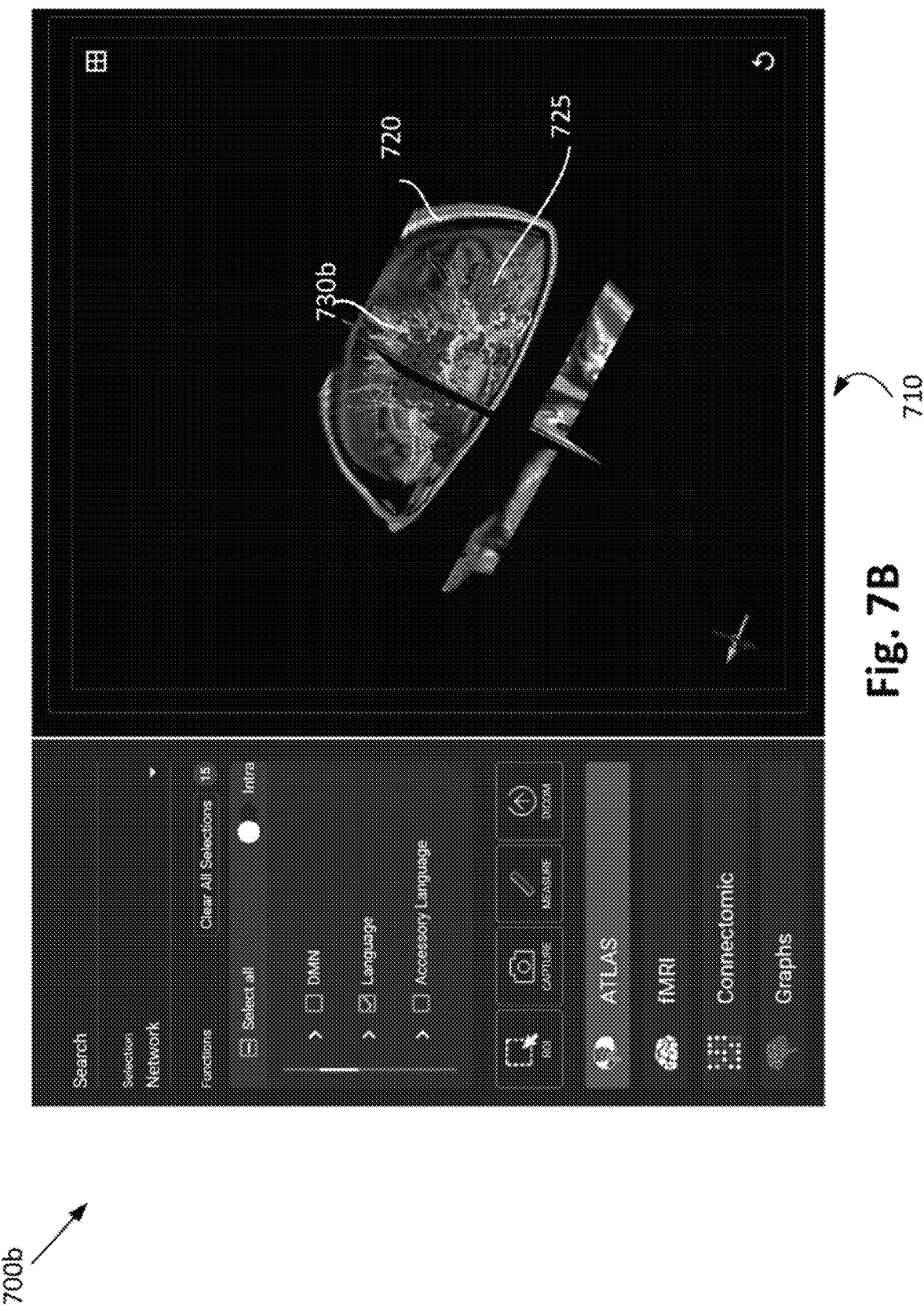
FIG. 7B shows the window of 7A showing a graphical representation of a selected network (e.g., the language network) of the subject brain.

In the arrangements described, the surface and/or selected tracts are rendered superimposed on the greyscale image corresponding to the T1 data of the MRI image. For example, FIG. 7B shows a window 700b reproduced by execution of the module 210. The window 700b reproduces a graphical representation of a network of a brain shown in FIG. 7A based on user selection of a Grouping "Network" and Level 1 "Language". In FIG. 7B, a graphical representation in the display area 710 includes a greyscale background 720 generated using the MRI image. In an alternative arrangement, a template image could be used as the background 720.

A number of surfaces (selected based on the user's menu selection and generated using the mesh surface 202) representing parcellations are overlaid on the greyscale image 720, such as a surface 725. The selected tracts from the DTI image are overlaid on the parcellation surfaces and the template, for example as indicated by 730b in the window 700b.

The step 430 can use known rendering methods, such as three.js or volume rendering using Visualization Toolkit (VTK), for example to render the tracts and the parcellation surface.

FIG. 5 shows a method 500 of selecting tracts as implemented at step 425 of the method 400. The method 500 is typically implemented as one or more modules of the application 210 stored in the memory 106 and controlled under execution of the processor 105.

The method 500 receives the coordinates determined in iterations of step 410 and the image data vectors determined at step 415. The method 500 starts at a determining step 505. Step 505 operates to determine a boundary for each parcellation indicated by the user selection received at step 315. The boundary is determined based on the surface mesh 202 associated with the parcellation. A similar method is used in step 430 to generate a surface for rendering, as described above.

The method 500 continues from step 505 to a determining step 510. Step 510 executes to determine intersections, also referred to as collisions, between of the image data with the generated surface. The intersections are determined based on modelling of operation of the subject brain over time using the DTI image data and known software such as TrackVis, DiPY (Diffusion MRI image package in Python) or Brainlab. One can store tracts and parcellations according to a different data model. Tracts can be stored as list of vectors with xyz coordinates for each point of each vector. One xyz coordinate can have multiple tracts. Parcellations can be stored in a simple tensor as only 1 parcellation id can be found for a given xyz coordinate. The "collision detection" or intersection can consist of scanning the full tract file for parcellations overlapping with tract specific xyz coordinates. The intersections determined at step 510 are in addition those determined to have corresponding coordinates at step 415.

The method 500 continues from step 510 to a check step 515. The step 515 operates to determine if more than one parcellation has been selected, as determined based on the number of parcellation identifiers determined at step 330. If only one parcellation has been selected ("N") at step 515, the method 500 continues to a selecting step 520. The step 520 executes to select all tracts intersecting or colliding with the selected parcellation surfaces.

If more than one parcellation has been selected ("Y" at step 515) the method 500 continues to a check step 525. Step 525 executes to check if "Intra" mode has been selected. Referring to FIG. 7, Intra mode is a display option that can be made by a user that is relevant when more than one parcellation in included in the selected network of the brain. A selectable intra button is show as 750, shown as turned off in the window 700. Intra mode determines whether all tracts colliding with selected parcellations are shown in the graphical representation of the network or only tracts beginning and ending in the selected parcellations are shown.

If Intra mode is selected ("Y") at step 525 the method 500 continues to a selecting step 530. Step 530 operates to select only tracts starting and ending in the selected parcellations.

If intra mode is off ("N" at step 525) the method 500 continues to a selecting step 535. Step 535 operates to select all tracts colliding with the selected parcellations irrespective of where the tracts start or end. In each of steps 520 and 535 the selected or determined tracts comprise all tracts intersecting regions associated with the parcellations determined from the user selection.

The method 500 ends after execution of any of steps 520, 530 and 535.

Figure 9A:
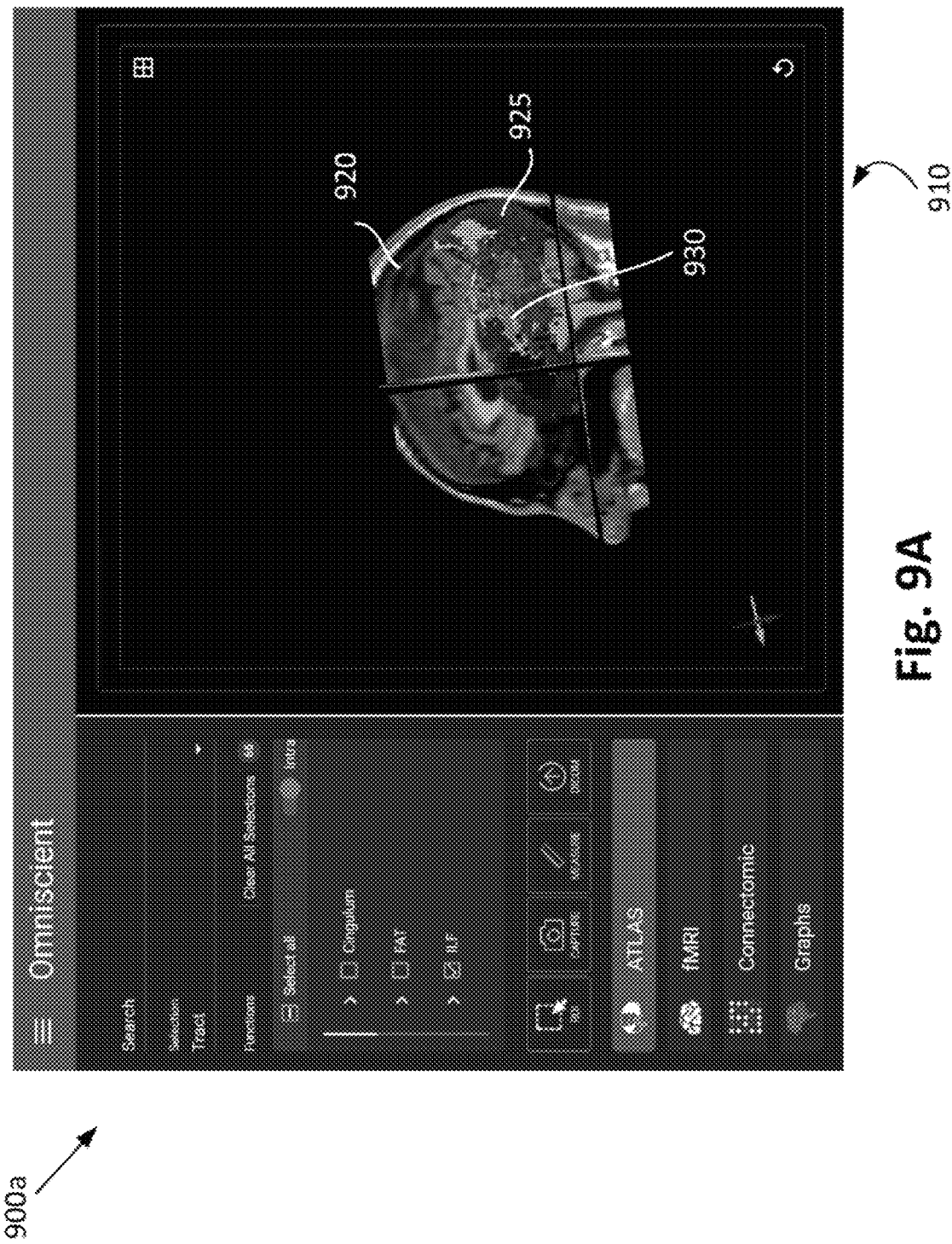
FIG. 9A shows a window of a graphical user interface showing a graphical representation of a network of a brain.

In another example, FIG. 9A shows a window 900a reproduced by execution of the module 210. The window 900a reproduces a graphical representation of a network of a brain based on user selection of a Grouping "Tract" and Level 1 "ILF" with Intra mode on. In FIG. 9A, a graphical representation in a display area 910 includes a greyscale background 920 generated using the MRI image. In an alternative arrangement, a template image could be used as the background 920.

A number of surfaces (selected based on the user's menu selection and generated using the mesh surface 202) representing parcellations are overlaid on the greyscale image 920, such as a surface 925. The selected tracts from the DTI image are overlaid on the parcellation surfaces and the template, for example indicated as 930 in the window 900a. In FIG. 9a both tracts and parcellations are shown, corresponding to checking of both 740 and 750 of FIG. 7A.

Figure 9B:
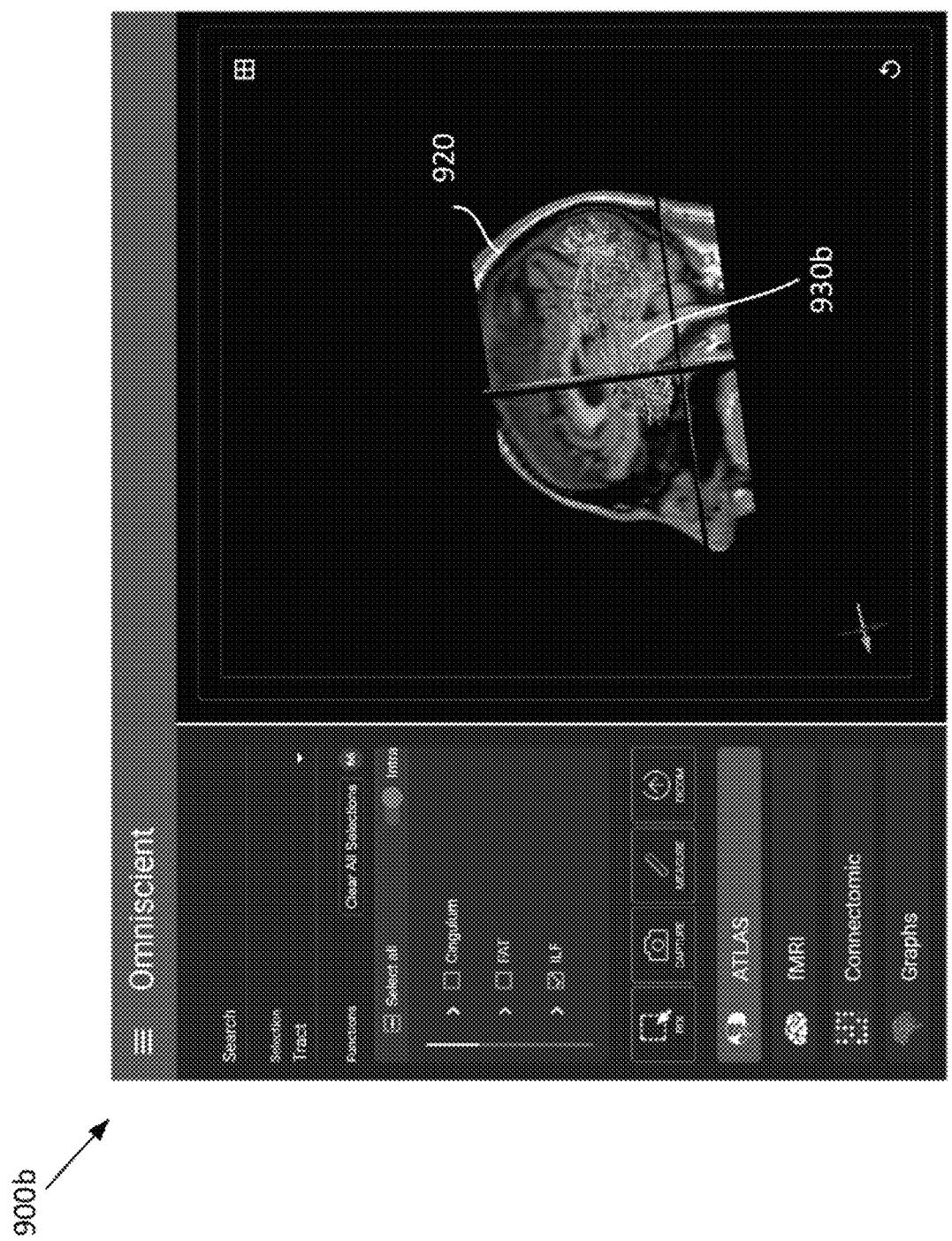
FIG. 9B shows the window of FIG. 9A updated to show a graphical representation of the network of a brain relating to tracts only.

FIG. 9B shows a window 900b reproduced by execution of the module 210. The window 900a reproduces a graphical representation of a network of a brain based on user selection of a Grouping "Tract" and Level 1 "ILF" with Intra mode on. In FIG. 9B only tracts 930b are shown over the greyscale image due selection of user display options (not shown). For example, using the example menu 720 of FIG. 7A, 740 would be checked and 750 unchecked.

Figure 6A:
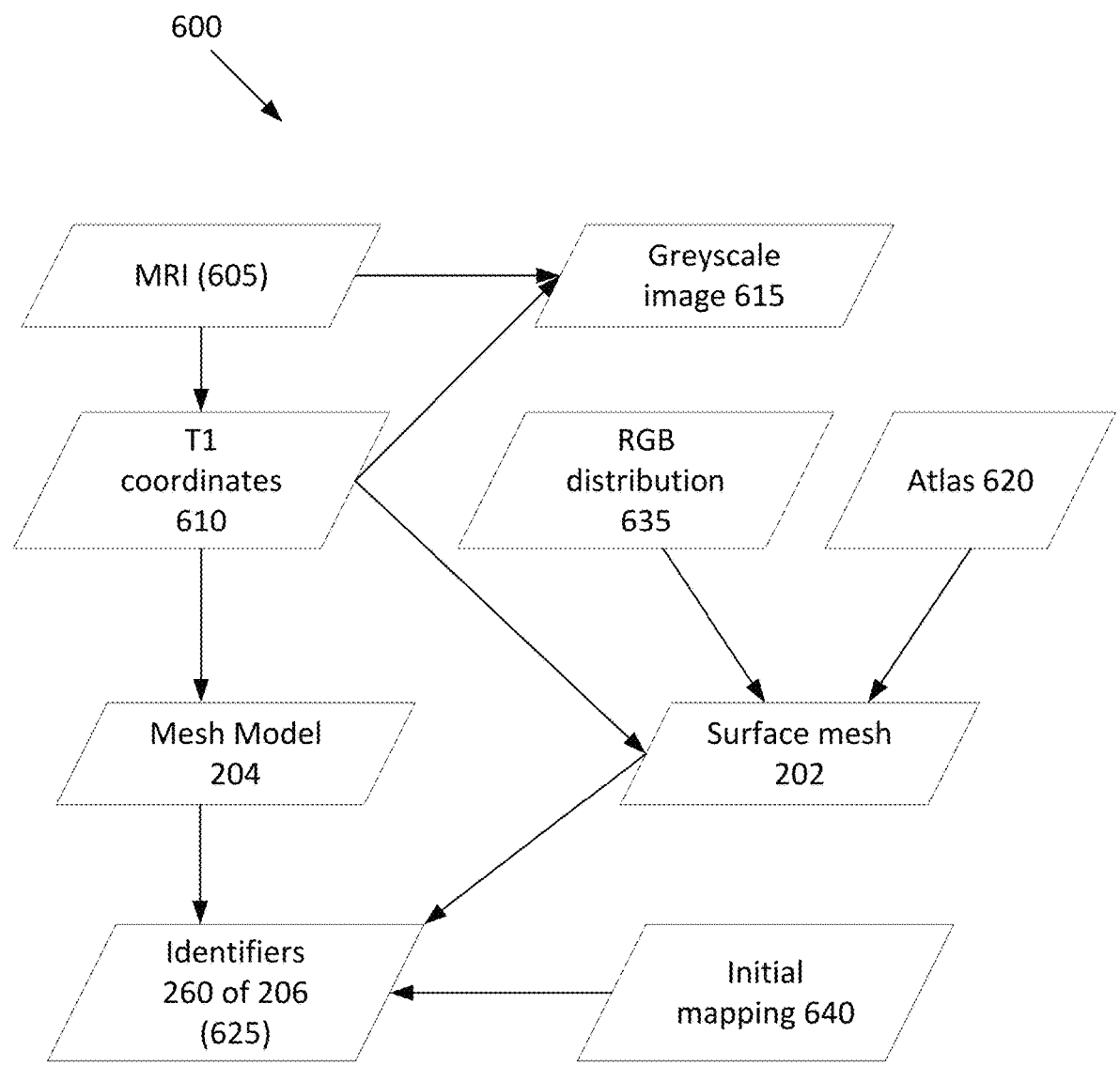
FIGS. 6A and 6B show dataflows of generating a graphical representation of a network of a subject human brain.

FIG. 6A shows a dataflow 600 associated with operation of step 307 of the method 300. The dataflow receives inputs of an MRI image 605 (as accessed at step 305), a brain atlas 620, an RGB distribution 635 and an initial mapping database 640. The brain atlas 620 can be a standard HCP-MMP atlas or another type of brain atlas. The RGB distribution 635 assigns RGB values to parcellations. The initial mapping database 640 relates to the data structure 250 in which parcellation identifiers have not yet been assigned for the subject brain.

The step 307 operates to use T1 data comprising three-dimensional coordinates 610 of the MRI image 610. The three-dimensional coordinates 610 in association with T1 greyscale data provide a greyscale image of the subject brain 615. Step 307 uses the coordinates 610 to creates the mesh model 204 comprising the coordinates 610 each having an associated mesh identifier.

The coordinates 610, the RGB distribution 635 and the atlas 620 are used to generate the surface mesh 202.

The dataflow 600 generates data 625, relating population of the identifiers 260 of the mapping database 206. The data 625 is generated based on the coordinates 610, the initial database 640 and the mesh model 204 such that the identifiers 260 correspond to identifiers in the same three-dimensional location of the mesh model 204. The mesh surface 202 and the mesh model 204 allow a parcellation name to be matched to a volume in space and the identifiers 260 to be populated accordingly.

Figure 6B:
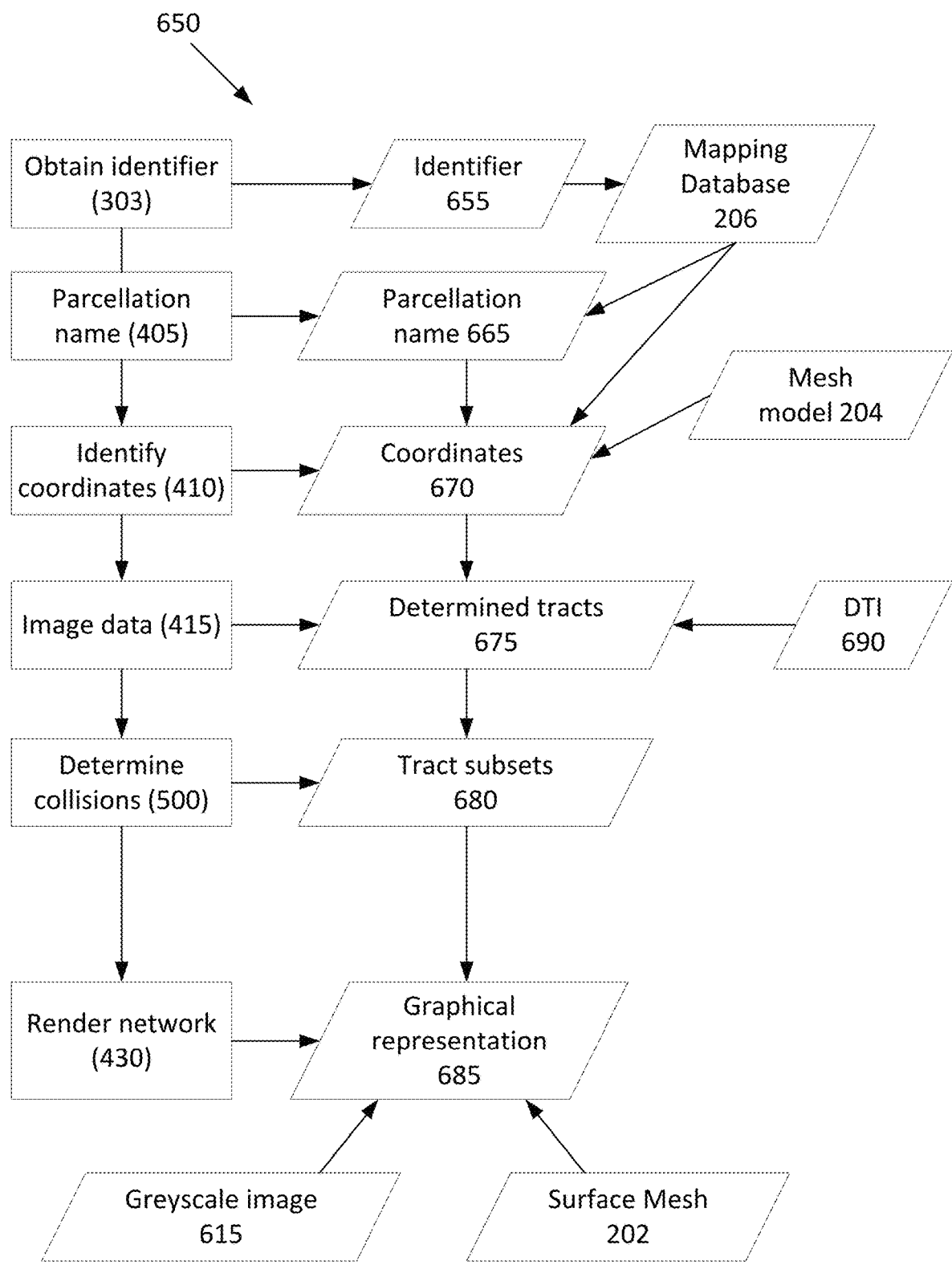

FIG. 6B shows a dataflow 650 associated with generating a graphical representation in terms of operation of FIGS. 3-5. As shown in the dataflow 650 a mesh identifier 655 is obtained in execution of step 303. The identifier 655 is used with the mapping database 206 to determine a parcellation name 665 (corresponding to 258) at step 405. Coordinates 670 for the identifier 655 are determined using the mesh model 204, the parcellation name 665 and the mapping database 206 at step 410.

The coordinates 670 and a DTI image 690 of the subject brain are used at step 415 to determine tract data 675 based on corresponding coordinates. The tract data relates to tracts as described in tract vector ((x, y, z)) form. A tract file can be a list of vectors in which each of the points constituting a vector are referenced in xyz coordinates. This approach can be used as a tract vector is not typically in a straight line. A subset of tracts 680 is determined in operation of the method 500 using the image 690 and the tract data 675. As described in relation to the method 500, the subset 680 may include all of the tracts 675 (steps 520 and 535) or tracts beginning and ending in selected parcellations only (step 530).

Step 430 operates to render a graphical representation 685 representing the user selection using the tract subsets 680, the greyscale image 615 and the surface mesh 202. A typical scan of a human brain can produce about 300,000 tracts. Each tract can have several hundreds of xyz coordinates.

As shown in FIG. 7A, graphical representation of the whole DTI image includes a high level of data that cannot be easily understood or divided into relevant portions. The graphical representation, although based on an actual captured image of the subject brain, provides limited clinical assistance to a viewer such as a neurosurgeon. However, generating a graphical representation of a network of the brain based using the arrangements described can result in images such as that shown in FIG. 7B. In FIG. 7B a neurosurgeon or other healthcare professional can identify relevant interconnections relating to language functions of the subject brain from the DTI image intuitively. The interconnections are relevant in terms of both structure and function of the selected network of the subject brain. The representation can be clinically more meaningful for the surgeon compared to a showing all tracts in a region, depending on the reason for analysis of the subject brain. Similarly, the examples of FIGS. 9A and 9B show networks relating to ILF only, and provide a more clinically meaningful image than current techniques.

Figure 10:
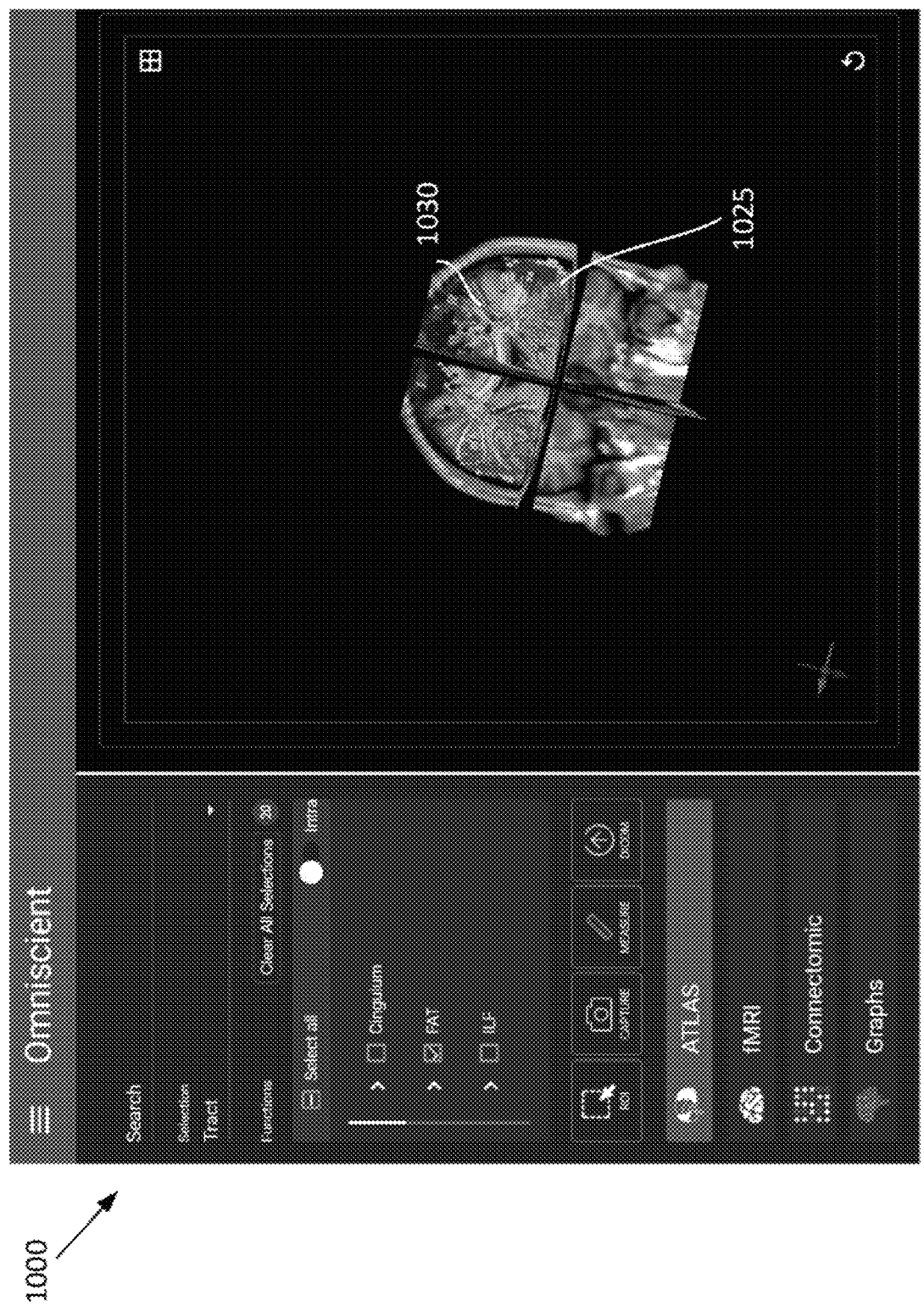
FIG. 10 shows another window of a graphical user interface showing a graphical representation of a network of a brain.

In a further example, FIG. 10 shows a window 1000 reproduced by execution of the module 210. The window 1000 reproduces a graphical representation of a network of a brain based on user selection of a Grouping "Tract" and Level 1 "FAT" with Intra mode off. The graphical representation includes surfaces representing parcellations (for example 1025) and tracts (1030) derived from a DTI image of the subject brain and determined to be related to structural parcellation FAT (frontal aslant tract).

The data structure 250 and use of parcellations allows a neurosurgeon or other neuroscience professional to select the relevant network of the brain intuitively. Further, the structure 250, mesh 204 and look up table 212 when used in combination allow the relevant portions of the DTI image to be determined for inclusion in the user-selected network.

The arrangements described are applicable to the medical image capture and data processing industries and particularly for the medical industries related to neurology and associated healthcare.

The foregoing describes only some embodiments of the present invention, and modifications and/or changes can be made thereto without departing from the scope and spirit of the invention, the embodiments being illustrative and not restrictive.

In the context of this specification, the word "comprising" means "including principally but not necessarily solely" or "having" or "including", and not "consisting only of". Variations of the word "comprising", such as "comprise" and "comprises" have correspondingly varied meanings.

TABLE 2

Example mapping database

| Grouping | Level 1 | Level 2 | Level 3 | Parcellation | ID |
|---|---|---|---|---|---|
| Network | Auditory | Left | Frontal | 44 | 74 |
| Network | Auditory | Left | Frontal | 8C | 73 |
| Network | Auditory | Left | Frontal | FOP4 | 108 |
| Network | Auditory | Right | Frontal | 44 | 274 |
| Network | Auditory | Right | Frontal | 8C | 273 |
| Network | Auditory | Right | Frontal | FOP4 | 308 |
| Network | Auditory | Left | Parietal | PFcm | 105 |
| Network | Auditory | Left | Parietal | PSL | 25 |
| Network | Auditory | Right | Parietal | PFcm | 305 |
| Network | Auditory | Right | Parietal | PSL | 225 |
| Network | Auditory | Left | SMA | SCEF | 43 |
| Network | Auditory | Right | SMA | SCEF | 243 |
| Network | Auditory | Left | Temporal | A1 | 24 |
| Network | Auditory | Left | Temporal | A4 | 175 |
| Network | Auditory | Left | Temporal | A5 | 125 |
| Network | Auditory | Left | Temporal | LBelt | 174 |
| Network | Auditory | Left | Temporal | MBelt | 173 |
| Network | Auditory | Left | Temporal | PBelt | 124 |
| Network | Auditory | Left | Temporal | RI | 104 |
| Network | Auditory | Left | Temporal | STSdp | 129 |
| Network | Auditory | Left | Temporal | TPOJ1 | 139 |
| Network | Auditory | Right | Temporal | A1 | 224 |
| Network | Auditory | Right | Temporal | A4 | 375 |
| Network | Auditory | Right | Temporal | A5 | 325 |
| Network | Auditory | Right | Temporal | LBelt | 374 |
| Network | Auditory | Right | Temporal | MBelt | 373 |
| Network | Auditory | Right | Temporal | PBelt | 324 |
| Network | Auditory | Right | Temporal | RI | 304 |
| Network | Auditory | Right | Temporal | STSdp | 329 |
| Network | Auditory | Right | Temporal | TPOJ1 | 339 |
| Network | CEN | Left | Frontal | 46 | 84 |
| Network | CEN | Left | Frontal | 8Ad | 68 |
| Network | CEN | Left | Frontal | 8Av | 67 |
| Network | CEN | Left | Frontal | a47r | 77 |
| Network | CEN | Left | Frontal | IFSa | 82 |
| Network | CEN | Left | Frontal | IFSp | 81 |
| Network | CEN | Left | Frontal | p47r | 171 |
| Network | CEN | Left | Frontal | p9-46v | 83 |
| Network | CEN | Right | Frontal | 46 | 284 |
| Network | CEN | Right | Frontal | 8Ad | 268 |
| Network | CEN | Right | Frontal | 8Av | 267 |
| Network | CEN | Right | Frontal | a47r | 277 |
| Network | CEN | Right | Frontal | IFSa | 282 |
| Network | CEN | Right | Frontal | IFSp | 281 |
| Network | CEN | Right | Frontal | p47r | 371 |
| Network | CEN | Right | Frontal | p9-46v | 283 |
| Network | CEN | Left | Parietal | AIP | 117 |
| Network | CEN | Left | Parietal | PF | 148 |
| Network | CEN | Left | Parietal | PFcm | 105 |
| Network | CEN | Left | Parietal | PFm | 149 |
| Network | CEN | Left | Parietal | PFt | 116 |
| Network | CEN | Left | Parietal | PSL | 25 |
| Network | CEN | Right | Parietal | AIP | 317 |
| Network | CEN | Right | Parietal | PF | 348 |
| Network | CEN | Right | Parietal | PFcm | 305 |
| Network | CEN | Right | Parietal | PFm | 349 |
| Network | CEN | Right | Parietal | PFt | 316 |
| Network | CEN | Right | Parietal | PSL | 225 |
| Network | DAN | Left | Dorsal Premotor | 6a | 96 |

TABLE 2-continued

Example mapping database

| Grouping | Level 1 | Level 2 | Level 3 | Parcellation | ID |
| --- | --- | --- | --- | --- | --- |
| Network | DAN | Right | Dorsal Premotor | 6a | 296 |
| Network | DAN | Left | Frontal | FEF | 10 |
| Network | DAN | Right | Frontal | FEF | 210 |
| Network | DAN | Left | Lateral Stream | MST | 2 |
| Network | DAN | Left | Lateral Stream | MT | 23 |
| Network | DAN | Left | Lateral Stream | PH | 138 |
| Network | DAN | Left | Lateral Stream | V4t | 156 |
| Network | DAN | Right | Lateral Stream | MST | 202 |
| Network | DAN | Right | Lateral Stream | MT | 223 |
| Network | DAN | Right | Lateral Stream | PH | 338 |
| Network | DAN | Right | Lateral Stream | V4t | 356 |
| Network | DAN | Left | Parietal | 7PC | 47 |
| Network | DAN | Left | Parietal | AIP | 117 |
| Network | DAN | Left | Parietal | LIPd | 95 |
| Network | DAN | Left | Parietal | LIPv | 48 |
| Network | DAN | Left | Parietal | VIP | 49 |
| Network | DAN | Right | Parietal | 7PC | 247 |
| Network | DAN | Right | Parietal | AIP | 317 |
| Network | DAN | Right | Parietal | LIPd | 295 |
| Network | DAN | Right | Parietal | LIPv | 248 |
| Network | DAN | Right | Parietal | VIP | 249 |
| Network | DMN | Left | ACC | 10r | 65 |
| Network | DMN | Left | ACC | a24 | 61 |
| Network | DMN | Left | ACC | p32 | 64 |
| Network | DMN | Left | ACC | s32 | 165 |
| Network | DMN | Right | ACC | 10r | 265 |
| Network | DMN | Right | ACC | a24 | 261 |
| Network | DMN | Right | ACC | p32 | 264 |
| Network | DMN | Right | ACC | s32 | 365 |
| Network | DMN | Left | Lateral Parietal | IP1 | 145 |
| Network | DMN | Left | Lateral Parietal | PGi | 150 |
| Network | DMN | Left | Lateral Parietal | PGs | 151 |
| Network | DMN | Left | Lateral Parietal | TPOJ3 | 141 |
| Network | DMN | Right | Lateral Parietal | IP1 | 345 |
| Network | DMN | Right | Lateral Parietal | PGi | 350 |
| Network | DMN | Right | Lateral Parietal | PGs | 351 |
| Network | DMN | Right | Lateral Parietal | TPOJ3 | 341 |
| Network | DMN | Left | PCC | 31a | 162 |
| Network | DMN | Left | PCC | 31pd | 161 |
| Network | DMN | Left | PCC | 31pv | 35 |
| Network | DMN | Left | PCC | d23ab | 34 |
| Network | DMN | Left | PCC | RSC | 14 |
| Network | DMN | Left | PCC | v23ab | 33 |
| Network | DMN | Right | PCC | 31a | 362 |
| Network | DMN | Right | PCC | 31pd | 361 |
| Network | DMN | Right | PCC | 31pv | 235 |
| Network | DMN | Right | PCC | d23ab | 234 |
| Network | DMN | Right | PCC | RSC | 214 |
| Network | DMN | Right | PCC | v23ab | 233 |
| Network | Language | Left | Frontal | 44 | 74 |
| Network | Language | Left | Frontal | 45 | 75 |
| Network | Language | Left | Frontal | 47l | 76 |
| Network | Language | Left | Frontal | 55b | 12 |
| Network | Language | Left | Frontal | 8C | 73 |
| Network | Language | Left | Frontal | IFJa | 79 |
| Network | Language | Left | Parietal | AIP | 117 |
| Network | Language | Left | Parietal | PFm | 149 |
| Network | Language | Left | SMA | SCEF | 43 |
| Network | Language | Left | SMA | SFL | 26 |
| Network | Language | Left | Temporal | PBelt | 124 |
| Network | Language | Left | Temporal | PHT | 137 |
| Network | Language | Left | Temporal | STSdp | 129 |
| Network | Language | Left | Temporal | STSvp | 130 |
| Network | Language | Left | Temporal | TE1p | 133 |
| Network | Accessory Language | Left | | STSda | 128 |
| Network | Accessory Language | Left | | STSva | 176 |
| Network | Accessory Language | Left | | TE1a | 132 |
| Network | Accessory Language | Left | | TGv | 172 |
| Network | Medial temporal | Left | Bilateral | EC | 118 |
| Network | Medial temporal | Left | Bilateral | PeEc | 122 |
| Network | Medial temporal | Left | Bilateral | PHA1 | 126 |
| Network | Medial temporal | Left | Bilateral | PHA2 | 155 |
| Network | Medial temporal | Left | Bilateral | PHA3 | 127 |
| Network | Medial temporal | Left | Bilateral | PreS | 119 |
| Network | Medial temporal | Right | Bilateral | EC | 318 |
| Network | Medial temporal | Right | Bilateral | PeEc | 322 |

TABLE 2-continued

Example mapping database

| Grouping | Level 1 | Level 2 | Level 3 | Parcellation | ID |
|---|---|---|---|---|---|
| Network | Medial temporal | Right | Bilateral | PHA1 | 326 |
| Network | Medial temporal | Right | Bilateral | PHA2 | 355 |
| Network | Medial temporal | Right | Bilateral | PHA3 | 327 |
| Network | Medial temporal | Right | Bilateral | PreS | 319 |
| Network | Medial temporal | Left | Subcortical | Amygdala | 418 |
| Network | Medial temporal | Left | Subcortical | Hippocampus | 417 |
| Network | Medial temporal | Right | Subcortical | Amygdala | 454 |
| Network | Medial temporal | Right | Subcortical | Hippocampus | 453 |
| Network | Neglect | Right | Frontal | 46 | 284 |
| Network | Neglect | Right | Frontal | FEF | 210 |
| Network | Neglect | Right | Frontal | p9-46v | 283 |
| Network | Neglect | Right | Parietal | AIP | 317 |
| Network | Neglect | Right | Parietal | PF | 348 |
| Network | Neglect | Right | Parietal | PFcm | 305 |
| Network | Neglect | Right | Parietal | PFt | 316 |
| Network | Neglect | Right | Primary | 4 | 208 |
| Network | Neglect | Right | Primary | 3a | 253 |
| Network | Neglect | Right | Temporal | A4 | 375 |
| Network | Neglect | Right | Temporal | LBelt | 374 |
| Network | Neglect | Right | Temporal | PBelt | 324 |
| Network | Neglect | Right | Temporal | STSdp | 329 |
| Network | Praxis | Left | Frontal | FOP4 | 108 |
| Network | Praxis | Left | Lateral Parietal | PGi | 150 |
| Network | Praxis | Left | Parietal | 52 | 103 |
| Network | Praxis | Left | Parietal | 7AL | 42 |
| Network | Praxis | Left | Parietal | 7PC | 47 |
| Network | Praxis | Left | Parietal | AIP | 117 |
| Network | Praxis | Left | Parietal | MIP | 50 |
| Network | Praxis | Left | Parietal | PFop | 147 |
| Network | Praxis | Left | Primary | 4 | 8 |
| Network | Praxis | Left | Primary | 3b | 9 |
| Network | Praxis | Left | SMA | SCEF | 43 |
| Network | Praxis | Left | Temporal | RI | 104 |
| Network | Salience | Left | Cingulate | a24pr | 59 |
| Network | Salience | Left | Cingulate | p32pr | 60 |
| Network | Salience | Right | Cingulate | a24pr | 259 |
| Network | Salience | Right | Cingulate | p32pr | 260 |
| Network | Salience | Left | Insula | AVI | 111 |
| Network | Salience | Left | Insula | FOP5 | 169 |
| Network | Salience | Left | Insula | MI | 109 |
| Network | Salience | Right | Insula | AVI | 311 |
| Network | Salience | Right | Insula | FOP5 | 369 |
| Network | Salience | Right | Insula | MI | 309 |
| Network | Sensorimotor | Left | Cingulate motor | 24dd | 40 |
| Network | Sensorimotor | Left | Cingulate motor | 24dv | 41 |
| Network | Sensorimotor | Right | Cingulate motor | 24dd | 240 |
| Network | Sensorimotor | Right | Cingulate motor | 24dv | 241 |
| Network | Sensorimotor | Left | Dorsal Premotor | 6a | 96 |
| Network | Sensorimotor | Left | Dorsal Premotor | 6d | 54 |
| Network | Sensorimotor | Right | Dorsal Premotor | 6a | 296 |
| Network | Sensorimotor | Right | Dorsal Premotor | 6d | 254 |
| Network | Sensorimotor | Left | Primary | 1 | 51 |
| Network | Sensorimotor | Left | Primary | 2 | 52 |
| Network | Sensorimotor | Left | Primary | 4 | 8 |
| Network | Sensorimotor | Left | Primary | 3a | 53 |
| Network | Sensorimotor | Left | Primary | 3b | 9 |
| Network | Sensorimotor | Right | Primary | 1 | 251 |
| Network | Sensorimotor | Right | Primary | 2 | 252 |
| Network | Sensorimotor | Right | Primary | 4 | 208 |
| Network | Sensorimotor | Right | Primary | 3a | 253 |
| Network | Sensorimotor | Right | Primary | 3b | 209 |
| Network | Sensorimotor | Left | SMA | 6ma | 44 |
| Network | Sensorimotor | Left | SMA | 6mp | 55 |
| Network | Sensorimotor | Left | SMA | SCEF | 43 |
| Network | Sensorimotor | Left | SMA | SFL | 26 |
| Network | Sensorimotor | Right | SMA | 6ma | 244 |
| Network | Sensorimotor | Right | SMA | 6mp | 255 |
| Network | Sensorimotor | Right | SMA | SCEF | 243 |
| Network | Sensorimotor | Right | SMA | SFL | 226 |
| Network | Sensorimotor | Left | Ventral Premotor | 6r | 78 |
| Network | Sensorimotor | Left | Ventral Premotor | 6v | 56 |
| Network | Sensorimotor | Right | Ventral Premotor | 6r | 278 |
| Network | Sensorimotor | Right | Ventral Premotor | 6v | 256 |
| Network | Subcortical | Left | Subcortical | Accumbens | 426 |
| Network | Subcortical | Left | Subcortical | Caudate | 411 |
| Network | Subcortical | Left | Subcortical | Cerebellum | 408 |

TABLE 2-continued

Example mapping database

| Grouping | Level 1 | Level 2 | Level 3 | Parcellation | ID |
|---|---|---|---|---|---|
| Network | Subcortical | Left | Subcortical | Pallidum | 413 |
| Network | Subcortical | Left | Subcortical | Putamen | 412 |
| Network | Subcortical | Left | Subcortical | Thalamus | 410 |
| Network | Subcortical | Left | Subcortical | VentralDC | 428 |
| Network | Subcortical | Right | Subcortical | Accumbens | 458 |
| Network | Subcortical | Right | Subcortical | Caudate | 450 |
| Network | Subcortical | Right | Subcortical | Cerebellum | 447 |
| Network | Subcortical | Right | Subcortical | Pallidum | 452 |
| Network | Subcortical | Right | Subcortical | Putamen | 451 |
| Network | Subcortical | Right | Subcortical | Thalamus | 449 |
| Network | Subcortical | Right | Subcortical | VentralDC | 460 |
| Network | VAN | Left | Dorsal Premotor | 6a | 96 |
| Network | VAN | Right | Dorsal Premotor | 6a | 296 |
| Network | VAN | Left | Frontal | 8C | 73 |
| Network | VAN | Left | Frontal | p9-46v | 83 |
| Network | VAN | Right | Frontal | 8C | 273 |
| Network | VAN | Right | Frontal | p9-46v | 283 |
| Network | VAN | Left | Inferior Parietal | TPOJ2 | 140 |
| Network | VAN | Left | Lateral Parietal | PGi | 150 |
| Network | VAN | Right | Lateral Parietal | PGi | 350 |
| Network | VAN | Left | Medial Parietal | PCV | 27 |
| Network | VAN | Left | Parietal | MIP | 50 |
| Network | VAN | Left | Parietal | PFm | 149 |
| Network | VAN | Right | Parietal | 7Am | 245 |
| Network | VAN | Right | Parietal | 7Pm | 229 |
| Network | VAN | Right | Parietal | MIP | 250 |
| Network | VAN | Right | Parietal | PCV | 227 |
| Network | VAN | Right | Parietal | PFm | 349 |
| Network | VAN | Right | Parietal | TPOJ2 | 340 |
| Network | VAN | Left | Superior Parietal | 7Am | 45 |
| Network | VAN | Left | Superior Parietal | 7Pm | 29 |
| Network | VAN | Left | Ventral Premotor | 6r | 78 |
| Network | VAN | Right | Ventral Premotor | 6r | 278 |
| Network | Visual | Left | Dorsal Stream | IPS1 | 17 |
| Network | Visual | Left | Dorsal Stream | V3A | 13 |
| Network | Visual | Left | Dorsal Stream | V3B | 19 |
| Network | Visual | Left | Dorsal Stream | V6 | 3 |
| Network | Visual | Left | Dorsal Stream | V6A | 152 |
| Network | Visual | Left | Dorsal Stream | V7 | 16 |
| Network | Visual | Right | Dorsal Stream | IPS1 | 217 |
| Network | Visual | Right | Dorsal Stream | V3A | 213 |
| Network | Visual | Right | Dorsal Stream | V3B | 219 |
| Network | Visual | Right | Dorsal Stream | V6 | 203 |
| Network | Visual | Right | Dorsal Stream | V6A | 352 |
| Network | Visual | Right | Dorsal Stream | V7 | 216 |
| Network | Visual | Left | Lateral Stream | FST | 157 |
| Network | Visual | Left | Lateral Stream | LO1 | 20 |
| Network | Visual | Left | Lateral Stream | LO2 | 21 |
| Network | Visual | Left | Lateral Stream | LO3 | 159 |
| Network | Visual | Left | Lateral Stream | MST | 2 |
| Network | Visual | Left | Lateral Stream | MT | 23 |
| Network | Visual | Left | Lateral Stream | PH | 138 |
| Network | Visual | Left | Lateral Stream | V3CD | 158 |
| Network | Visual | Left | Lateral Stream | V4t | 156 |
| Network | Visual | Right | Lateral Stream | FST | 357 |
| Network | Visual | Right | Lateral Stream | LO1 | 220 |
| Network | Visual | Right | Lateral Stream | LO2 | 221 |
| Network | Visual | Right | Lateral Stream | LO3 | 359 |
| Network | Visual | Right | Lateral Stream | MST | 202 |
| Network | Visual | Right | Lateral Stream | MT | 223 |
| Network | Visual | Right | Lateral Stream | PH | 338 |
| Network | Visual | Right | Lateral Stream | V3CD | 358 |
| Network | Visual | Right | Lateral Stream | V4t | 356 |
| Network | Visual | Left | Medial | V1 | 1 |
| Network | Visual | Left | Medial | V2 | 4 |
| Network | Visual | Left | Medial | V3 | 5 |
| Network | Visual | Left | Medial | V4 | 6 |
| Network | Visual | Right | Medial | V1 | 201 |
| Network | Visual | Right | Medial | V2 | 204 |
| Network | Visual | Right | Medial | V3 | 205 |
| Network | Visual | Right | Medial | V4 | 206 |
| Network | Visual | Left | Ventral Stream | FFC | 18 |
| Network | Visual | Left | Ventral Stream | PIT | 22 |
| Network | Visual | Left | Ventral Stream | V8 | 7 |
| Network | Visual | Left | Ventral Stream | VMV1 | 153 |
| Network | Visual | Left | Ventral Stream | VMV2 | 160 |

TABLE 2-continued

Example mapping database

| Grouping | Level 1 | Level 2 | Level 3 | Parcellation | ID |
|---|---|---|---|---|---|
| Network | Visual | Left | Ventral Stream | VMV3 | 154 |
| Network | Visual | Left | Ventral Stream | VVC | 163 |
| Network | Visual | Right | Ventral Stream | FFC | 218 |
| Network | Visual | Right | Ventral Stream | PIT | 222 |
| Network | Visual | Right | Ventral Stream | V8 | 207 |
| Network | Visual | Right | Ventral Stream | VMV1 | 353 |
| Network | Visual | Right | Ventral Stream | VMV2 | 360 |
| Network | Visual | Right | Ventral Stream | VMV3 | 354 |
| Network | Visual | Right | Ventral Stream | VVC | 363 |
| Parcellation | | Left | Subcortical | Accumbens | 426 |
| Parcellation | | Left | Subcortical | Amygdala | 418 |
| Parcellation | | Left | Subcortical | Caudate | 411 |
| Parcellation | | Left | Subcortical | Cerebellum | 408 |
| Parcellation | | Left | Subcortical | Hippocampus | 417 |
| Parcellation | | Left | Subcortical | Pallidum | 413 |
| Parcellation | | Left | Subcortical | Putamen | 412 |
| Parcellation | | Left | Subcortical | Thalamus | 410 |
| Parcellation | | Left | Subcortical | VentralDC | 428 |
| Parcellation | | Right | Subcortical | Accumbens | 458 |
| Parcellation | | Right | Subcortical | Amygdala | 454 |
| Parcellation | | Right | Subcortical | Caudate | 450 |
| Parcellation | | Right | Subcortical | Cerebellum | 447 |
| Parcellation | | Right | Subcortical | Hippocampus | 453 |
| Parcellation | | Right | Subcortical | Pallidum | 452 |
| Parcellation | | Right | Subcortical | Putamen | 451 |
| Parcellation | | Right | Subcortical | Thalamus | 449 |
| Parcellation | | Right | Subcortical | VentralDC | 460 |
| Parcellation | | | Subcortical | Brain-Stem | 416 |
| Parcellation | | Left | | 1 | 51 |
| Parcellation | | Left | | 2 | 52 |
| Parcellation | | Left | | 4 | 8 |
| Parcellation | | Left | | 25 | 164 |
| Parcellation | | Left | | 43 | 99 |
| Parcellation | | Left | | 44 | 74 |
| Parcellation | | Left | | 45 | 75 |
| Parcellation | | Left | | 46 | 84 |
| Parcellation | | Left | | 52 | 103 |
| Parcellation | | Left | | 10d | 72 |
| Parcellation | | Left | | 10pp | 90 |
| Parcellation | | Left | | 10r | 65 |
| Parcellation | | Left | | 10v | 88 |
| Parcellation | | Left | | 111 | 91 |
| Parcellation | | Left | | 13l | 92 |
| Parcellation | | Left | | 23c | 38 |
| Parcellation | | Left | | 23d | 32 |
| Parcellation | | Left | | 24dd | 40 |
| Parcellation | | Left | | 24dv | 41 |
| Parcellation | | Left | | 31a | 162 |
| Parcellation | | Left | | 31pd | 161 |
| Parcellation | | Left | | 31pv | 35 |
| Parcellation | | Left | | 33pr | 58 |
| Parcellation | | Left | | 3a | 53 |
| Parcellation | | Left | | 3b | 9 |
| Parcellation | | Left | | 47l | 76 |
| Parcellation | | Left | | 47m | 66 |
| Parcellation | | Left | | 47s | 94 |
| Parcellation | | Left | | 55b | 12 |
| Parcellation | | Left | | 5L | 39 |
| Parcellation | | Left | | 5m | 36 |
| Parcellation | | Left | | 5mv | 37 |
| Parcellation | | Left | | 6a | 96 |
| Parcellation | | Left | | 6d | 54 |
| Parcellation | | Left | | 6ma | 44 |
| Parcellation | | Left | | 6mp | 55 |
| Parcellation | | Left | | 6r | 78 |
| Parcellation | | Left | | 6v | 56 |
| Parcellation | | Left | | 7AL | 42 |
| Parcellation | | Left | | 7Am | 45 |
| Parcellation | | Left | | 7m | 30 |
| Parcellation | | Left | | 7PC | 47 |
| Parcellation | | Left | | 7PL | 46 |
| Parcellation | | Left | | 7Pm | 29 |
| Parcellation | | Left | | 8Ad | 68 |
| Parcellation | | Left | | 8Av | 67 |
| Parcellation | | Left | | 8BL | 70 |
| Parcellation | | Left | | 8BM | 63 |

TABLE 2-continued

Example mapping database

| Grouping | Level 1 | Level 2 | Level 3 | Parcellation | ID |
|---|---|---|---|---|---|
| Parcellation | | Left | | 8C | 73 |
| Parcellation | | Left | | 9-46d | 86 |
| Parcellation | | Left | | 9a | 87 |
| Parcellation | | Left | | 9m | 69 |
| Parcellation | | Left | | 9p | 71 |
| Parcellation | | Left | | A1 | 24 |
| Parcellation | | Left | | a10p | 89 |
| Parcellation | | Left | | a24 | 61 |
| Parcellation | | Left | | a24pr | 59 |
| Parcellation | | Left | | a32pr | 179 |
| Parcellation | | Left | | A4 | 175 |
| Parcellation | | Left | | a47r | 77 |
| Parcellation | | Left | | A5 | 125 |
| Parcellation | | Left | | a9-46v | 85 |
| Parcellation | | Left | | AAIC | 112 |
| Parcellation | | Left | | AIP | 117 |
| Parcellation | | Left | | AVI | 111 |
| Parcellation | | Left | | d23ab | 34 |
| Parcellation | | Left | | d32 | 62 |
| Parcellation | | Left | | DVT | 142 |
| Parcellation | | Left | | EC | 118 |
| Parcellation | | Left | | FEF | 10 |
| Parcellation | | Left | | FFC | 18 |
| Parcellation | | Left | | FOP1 | 113 |
| Parcellation | | Left | | FOP2 | 115 |
| Parcellation | | Left | | FOP3 | 114 |
| Parcellation | | Left | | FOP4 | 108 |
| Parcellation | | Left | | FOP5 | 169 |
| Parcellation | | Left | | FST | 157 |
| Parcellation | | Left | | H | 120 |
| Parcellation | | Left | | i6-8 | 97 |
| Parcellation | | Left | | IFJa | 79 |
| Parcellation | | Left | | IFJp | 80 |
| Parcellation | | Left | | IFSa | 82 |
| Parcellation | | Left | | IFSp | 81 |
| Parcellation | | Left | | Ig | 168 |
| Parcellation | | Left | | IP0 | 146 |
| Parcellation | | Left | | IP1 | 145 |
| Parcellation | | Left | | IP2 | 144 |
| Parcellation | | Left | | IPS1 | 17 |
| Parcellation | | Left | | LBelt | 174 |
| Parcellation | | Left | | LIPd | 95 |
| Parcellation | | Left | | LIPv | 48 |
| Parcellation | | Left | | LO1 | 20 |
| Parcellation | | Left | | LO2 | 21 |
| Parcellation | | Left | | LO3 | 159 |
| Parcellation | | Left | | MBelt | 173 |
| Parcellation | | Left | | MI | 109 |
| Parcellation | | Left | | MIP | 50 |
| Parcellation | | Left | | MST | 2 |
| Parcellation | | Left | | MT | 23 |
| Parcellation | | Left | | OFC | 93 |
| Parcellation | | Left | | OP1 | 101 |
| Parcellation | | Left | | OP2-3 | 102 |
| Parcellation | | Left | | OP4 | 100 |
| Parcellation | | Left | | p10p | 170 |
| Parcellation | | Left | | p24 | 180 |
| Parcellation | | Left | | p24pr | 57 |
| Parcellation | | Left | | p32 | 64 |
| Parcellation | | Left | | p32pr | 60 |
| Parcellation | | Left | | p47r | 171 |
| Parcellation | | Left | | p9-46v | 83 |
| Parcellation | | Left | | PBelt | 124 |
| Parcellation | | Left | | PCV | 27 |
| Parcellation | | Left | | PeEc | 122 |
| Parcellation | | Left | | PEF | 11 |
| Parcellation | | Left | | PF | 148 |
| Parcellation | | Left | | PFcm | 105 |
| Parcellation | | Left | | PFm | 149 |
| Parcellation | | Left | | PFop | 147 |
| Parcellation | | Left | | PFt | 116 |
| Parcellation | | Left | | PGi | 150 |
| Parcellation | | Left | | PGp | 143 |
| Parcellation | | Left | | PGs | 151 |
| Parcellation | | Left | | PH | 138 |
| Parcellation | | Left | | PHA1 | 126 |

TABLE 2-continued

Example mapping database

| Grouping | Level 1 | Level 2 | Level 3 | Parcellation | ID |
|---|---|---|---|---|---|
| Parcellation | | Left | | PHA2 | 155 |
| Parcellation | | Left | | PHA3 | 127 |
| Parcellation | | Left | | PHT | 137 |
| Parcellation | | Left | | PI | 178 |
| Parcellation | | Left | | Pir | 110 |
| Parcellation | | Left | | PIT | 22 |
| Parcellation | | Left | | pOFC | 166 |
| Parcellation | | Left | | PoI1 | 167 |
| Parcellation | | Left | | PoI2 | 106 |
| Parcellation | | Left | | POS1 | 31 |
| Parcellation | | Left | | POS2 | 15 |
| Parcellation | | Left | | PreS | 119 |
| Parcellation | | Left | | ProS | 121 |
| Parcellation | | Left | | PSL | 25 |
| Parcellation | | Left | | RI | 104 |
| Parcellation | | Left | | RSC | 14 |
| Parcellation | | Left | | s32 | 165 |
| Parcellation | | Left | | s6-8 | 98 |
| Parcellation | | Left | | SCEF | 43 |
| Parcellation | | Left | | SFL | 26 |
| Parcellation | | Left | | STGa | 123 |
| Parcellation | | Left | | STSda | 128 |
| Parcellation | | Left | | STSdp | 129 |
| Parcellation | | Left | | STSva | 176 |
| Parcellation | | Left | | STSvp | 130 |
| Parcellation | | Left | | STV | 28 |
| Parcellation | | Left | | TA2 | 107 |
| Parcellation | | Left | | TE1a | 132 |
| Parcellation | | Left | | TE1m | 177 |
| Parcellation | | Left | | TE1p | 133 |
| Parcellation | | Left | | TE2a | 134 |
| Parcellation | | Left | | TE2p | 136 |
| Parcellation | | Left | | TF | 135 |
| Parcellation | | Left | | TGd | 131 |
| Parcellation | | Left | | TGv | 172 |
| Parcellation | | Left | | TPOJ1 | 139 |
| Parcellation | | Left | | TPOJ2 | 140 |
| Parcellation | | Left | | TPOJ3 | 141 |
| Parcellation | | Left | | V1 | 1 |
| Parcellation | | Left | | V2 | 4 |
| Parcellation | | Left | | v23ab | 33 |
| Parcellation | | Left | | V3 | 5 |
| Parcellation | | Left | | V3A | 13 |
| Parcellation | | Left | | V3B | 19 |
| Parcellation | | Left | | V3CD | 158 |
| Parcellation | | Left | | V4 | 6 |
| Parcellation | | Left | | V4t | 156 |
| Parcellation | | Left | | V6 | 3 |
| Parcellation | | Left | | V6A | 152 |
| Parcellation | | Left | | V7 | 16 |
| Parcellation | | Left | | V8 | 7 |
| Parcellation | | Left | | VIP | 49 |
| Parcellation | | Left | | VMV1 | 153 |
| Parcellation | | Left | | VMV2 | 160 |
| Parcellation | | Left | | VMV3 | 154 |
| Parcellation | | Left | | VVC | 163 |
| Parcellation | | Right | | 1 | 251 |
| Parcellation | | Right | | 2 | 252 |
| Parcellation | | Right | | 4 | 208 |
| Parcellation | | Right | | 25 | 364 |
| Parcellation | | Right | | 43 | 299 |
| Parcellation | | Right | | 44 | 274 |
| Parcellation | | Right | | 45 | 275 |
| Parcellation | | Right | | 46 | 284 |
| Parcellation | | Right | | 52 | 303 |
| Parcellation | | Right | | 10d | 272 |
| Parcellation | | Right | | 10pp | 290 |
| Parcellation | | Right | | 10r | 265 |
| Parcellation | | Right | | 10v | 288 |
| Parcellation | | Right | | 11l | 291 |
| Parcellation | | Right | | 13l | 292 |
| Parcellation | | Right | | 23c | 238 |
| Parcellation | | Right | | 23d | 232 |
| Parcellation | | Right | | 24dd | 240 |
| Parcellation | | Right | | 24dv | 241 |
| Parcellation | | Right | | 31a | 362 |

TABLE 2-continued

Example mapping database

| Grouping | Level 1 | Level 2 | Level 3 | Parcellation | ID |
|---|---|---|---|---|---|
| Parcellation | | Right | | 31pd | 361 |
| Parcellation | | Right | | 31pv | 235 |
| Parcellation | | Right | | 33pr | 258 |
| Parcellation | | Right | | 3a | 253 |
| Parcellation | | Right | | 3b | 209 |
| Parcellation | | Right | | 47l | 276 |
| Parcellation | | Right | | 47m | 266 |
| Parcellation | | Right | | 47s | 294 |
| Parcellation | | Right | | 55b | 212 |
| Parcellation | | Right | | 5L | 239 |
| Parcellation | | Right | | 5m | 236 |
| Parcellation | | Right | | 5mv | 237 |
| Parcellation | | Right | | 6a | 296 |
| Parcellation | | Right | | 6d | 254 |
| Parcellation | | Right | | 6ma | 244 |
| Parcellation | | Right | | 6mp | 255 |
| Parcellation | | Right | | 6r | 278 |
| Parcellation | | Right | | 6v | 256 |
| Parcellation | | Right | | 7AL | 242 |
| Parcellation | | Right | | 7Am | 245 |
| Parcellation | | Right | | 7m | 230 |
| Parcellation | | Right | | 7PC | 247 |
| Parcellation | | Right | | 7PL | 246 |
| Parcellation | | Right | | 7Pm | 229 |
| Parcellation | | Right | | 8Ad | 268 |
| Parcellation | | Right | | 8Av | 267 |
| Parcellation | | Right | | 8BL | 270 |
| Parcellation | | Right | | 8BM | 263 |
| Parcellation | | Right | | 8C | 273 |
| Parcellation | | Right | | 9-46d | 286 |
| Parcellation | | Right | | 9a | 287 |
| Parcellation | | Right | | 9m | 269 |
| Parcellation | | Right | | 9p | 271 |
| Parcellation | | Right | | A1 | 224 |
| Parcellation | | Right | | a10p | 289 |
| Parcellation | | Right | | a24 | 261 |
| Parcellation | | Right | | a24pr | 259 |
| Parcellation | | Right | | a32pr | 379 |
| Parcellation | | Right | | A4 | 375 |
| Parcellation | | Right | | a47r | 277 |
| Parcellation | | Right | | A5 | 325 |
| Parcellation | | Right | | a9-46v | 285 |
| Parcellation | | Right | | AAIC | 312 |
| Parcellation | | Right | | AIP | 317 |
| Parcellation | | Right | | AVI | 311 |
| Parcellation | | Right | | d23ab | 234 |
| Parcellation | | Right | | d32 | 262 |
| Parcellation | | Right | | DVT | 342 |
| Parcellation | | Right | | EC | 318 |
| Parcellation | | Right | | FEF | 210 |
| Parcellation | | Right | | FFC | 218 |
| Parcellation | | Right | | FOP1 | 313 |
| Parcellation | | Right | | FOP2 | 315 |
| Parcellation | | Right | | FOP3 | 314 |
| Parcellation | | Right | | FOP4 | 308 |
| Parcellation | | Right | | FOP5 | 369 |
| Parcellation | | Right | | FST | 357 |
| Parcellation | | Right | | H | 320 |
| Parcellation | | Right | | i6-8 | 297 |
| Parcellation | | Right | | IFJa | 279 |
| Parcellation | | Right | | IFJp | 280 |
| Parcellation | | Right | | IFSa | 282 |
| Parcellation | | Right | | IFSp | 281 |
| Parcellation | | Right | | Ig | 368 |
| Parcellation | | Right | | IP0 | 346 |
| Parcellation | | Right | | IP1 | 345 |
| Parcellation | | Right | | IP2 | 344 |
| Parcellation | | Right | | IPS1 | 217 |
| Parcellation | | Right | | LBelt | 374 |
| Parcellation | | Right | | LIPd | 295 |
| Parcellation | | Right | | LIPv | 248 |
| Parcellation | | Right | | LO1 | 220 |
| Parcellation | | Right | | LO2 | 221 |
| Parcellation | | Right | | LO3 | 359 |
| Parcellation | | Right | | MBelt | 373 |
| Parcellation | | Right | | MI | 309 |

TABLE 2-continued

Example mapping database

| Grouping | Level 1 | Level 2 | Level 3 | Parcellation | ID |
|---|---|---|---|---|---|
| Parcellation | | Right | | MIP | 250 |
| Parcellation | | Right | | MST | 202 |
| Parcellation | | Right | | MT | 223 |
| Parcellation | | Right | | OFC | 293 |
| Parcellation | | Right | | OP1 | 301 |
| Parcellation | | Right | | OP2-3 | 302 |
| Parcellation | | Right | | OP4 | 300 |
| Parcellation | | Right | | p10p | 370 |
| Parcellation | | Right | | p24 | 380 |
| Parcellation | | Right | | p24pr | 257 |
| Parcellation | | Right | | p32 | 264 |
| Parcellation | | Right | | p32pr | 260 |
| Parcellation | | Right | | p47r | 371 |
| Parcellation | | Right | | p9-46v | 283 |
| Parcellation | | Right | | PBelt | 324 |
| Parcellation | | Right | | PCV | 227 |
| Parcellation | | Right | | PeEc | 322 |
| Parcellation | | Right | | PEF | 211 |
| Parcellation | | Right | | PF | 348 |
| Parcellation | | Right | | PFcm | 305 |
| Parcellation | | Right | | PFm | 349 |
| Parcellation | | Right | | PFop | 347 |
| Parcellation | | Right | | PFt | 316 |
| Parcellation | | Right | | PGi | 350 |
| Parcellation | | Right | | PGp | 343 |
| Parcellation | | Right | | PGs | 351 |
| Parcellation | | Right | | PH | 338 |
| Parcellation | | Right | | PHA1 | 326 |
| Parcellation | | Right | | PHA2 | 355 |
| Parcellation | | Right | | PHA3 | 327 |
| Parcellation | | Right | | PHT | 337 |
| Parcellation | | Right | | PI | 378 |
| Parcellation | | Right | | Pir | 310 |
| Parcellation | | Right | | PIT | 222 |
| Parcellation | | Right | | pOFC | 366 |
| Parcellation | | Right | | PoI1 | 367 |
| Parcellation | | Right | | PoI2 | 306 |
| Parcellation | | Right | | POS1 | 231 |
| Parcellation | | Right | | POS2 | 215 |
| Parcellation | | Right | | PreS | 319 |
| Parcellation | | Right | | ProS | 321 |
| Parcellation | | Right | | PSL | 225 |
| Parcellation | | Right | | RI | 304 |
| Parcellation | | Right | | RSC | 214 |
| Parcellation | | Right | | s32 | 365 |
| Parcellation | | Right | | s6-8 | 298 |
| Parcellation | | Right | | SCEF | 243 |
| Parcellation | | Right | | SFL | 226 |
| Parcellation | | Right | | STGa | 323 |
| Parcellation | | Right | | STSda | 328 |
| Parcellation | | Right | | STSdp | 329 |
| Parcellation | | Right | | STSva | 376 |
| Parcellation | | Right | | STSvp | 330 |
| Parcellation | | Right | | STV | 228 |
| Parcellation | | Right | | TA2 | 307 |
| Parcellation | | Right | | TE1a | 332 |
| Parcellation | | Right | | TE1m | 377 |
| Parcellation | | Right | | TE1p | 333 |
| Parcellation | | Right | | TE2a | 334 |
| Parcellation | | Right | | TE2p | 336 |
| Parcellation | | Right | | TF | 335 |
| Parcellation | | Right | | TGd | 331 |
| Parcellation | | Right | | TGv | 372 |
| Parcellation | | Right | | TPOJ1 | 339 |
| Parcellation | | Right | | TPOJ2 | 340 |
| Parcellation | | Right | | TPOJ3 | 341 |
| Parcellation | | Right | | V1 | 201 |
| Parcellation | | Right | | V2 | 204 |
| Parcellation | | Right | | v23ab | 233 |
| Parcellation | | Right | | V3 | 205 |
| Parcellation | | Right | | V3A | 213 |
| Parcellation | | Right | | V3B | 219 |
| Parcellation | | Right | | V3CD | 358 |
| Parcellation | | Right | | V4 | 206 |
| Parcellation | | Right | | V4t | 356 |
| Parcellation | | Right | | V6 | 203 |

TABLE 2-continued

Example mapping database

| Grouping | Level 1 | Level 2 | Level 3 | Parcellation | ID |
|---|---|---|---|---|---|
| Parcellation | | Right | | V6A | 352 |
| Parcellation | | Right | | V7 | 216 |
| Parcellation | | Right | | V8 | 207 |
| Parcellation | | Right | | VIP | 249 |
| Parcellation | | Right | | VMV1 | 353 |
| Parcellation | | Right | | VMV2 | 360 |
| Parcellation | | Right | | VMV3 | 354 |
| Parcellation | | Right | | VVC | 363 |
| Tract | Cingulum | Left | ACC | 10r | 65 |
| Tract | Cingulum | Left | ACC | a24 | 61 |
| Tract | Cingulum | Left | ACC | p32 | 64 |
| Tract | Cingulum | Left | ACC | s32 | 165 |
| Tract | Cingulum | Right | ACC | 10r | 265 |
| Tract | Cingulum | Right | ACC | a24 | 261 |
| Tract | Cingulum | Right | ACC | p32 | 264 |
| Tract | Cingulum | Right | ACC | s32 | 365 |
| Tract | Cingulum | Left | Bilateral | EC | 118 |
| Tract | Cingulum | Left | Bilateral | PeEc | 122 |
| Tract | Cingulum | Left | Bilateral | PreS | 119 |
| Tract | Cingulum | Right | Bilateral | EC | 318 |
| Tract | Cingulum | Right | Bilateral | PeEc | 322 |
| Tract | Cingulum | Right | Bilateral | PreS | 319 |
| Tract | Cingulum | Left | Cingulate | a24pr | 59 |
| Tract | Cingulum | Left | Cingulate | p32pr | 60 |
| Tract | Cingulum | Right | Cingulate | a24pr | 259 |
| Tract | Cingulum | Right | Cingulate | p32pr | 260 |
| Tract | Cingulum | Left | Dorsal Stream | V6 | 3 |
| Tract | Cingulum | Right | Dorsal Stream | V6 | 203 |
| Tract | Cingulum | Left | Frontopolar | 10d | 72 |
| Tract | Cingulum | Right | Frontopolar | 10d | 272 |
| Tract | Cingulum | Left | Medial | V1 | 1 |
| Tract | Cingulum | Left | Medial | V2 | 4 |
| Tract | Cingulum | Right | Medial | V1 | 201 |
| Tract | Cingulum | Right | Medial | V2 | 204 |
| Tract | Cingulum | Left | Medial Frontal | 25 | 164 |
| Tract | Cingulum | Left | Medial Frontal | 33pr | 58 |
| Tract | Cingulum | Left | Medial Frontal | 8BM | 63 |
| Tract | Cingulum | Left | Medial Frontal | 9m | 69 |
| Tract | Cingulum | Left | Medial Frontal | a32pr | 179 |
| Tract | Cingulum | Left | Medial Frontal | d32 | 62 |
| Tract | Cingulum | Left | Medial Frontal | p24 | 180 |
| Tract | Cingulum | Left | Medial Frontal | p24pr | 57 |
| Tract | Cingulum | Right | Medial Frontal | 25 | 364 |
| Tract | Cingulum | Right | Medial Frontal | 33pr | 258 |
| Tract | Cingulum | Right | Medial Frontal | 8BM | 263 |
| Tract | Cingulum | Right | Medial Frontal | 9m | 269 |
| Tract | Cingulum | Right | Medial Frontal | a32pr | 379 |
| Tract | Cingulum | Right | Medial Frontal | d32 | 262 |
| Tract | Cingulum | Right | Medial Frontal | p24 | 380 |
| Tract | Cingulum | Right | Medial Frontal | p24pr | 257 |
| Tract | Cingulum | Left | Medial Parietal | 23c | 38 |
| Tract | Cingulum | Left | Medial Parietal | 23d | 32 |
| Tract | Cingulum | Left | Medial Parietal | 7m | 30 |
| Tract | Cingulum | Left | Medial Parietal | DVT | 142 |
| Tract | Cingulum | Left | Medial Parietal | PCV | 27 |
| Tract | Cingulum | Left | Medial Parietal | POS1 | 31 |
| Tract | Cingulum | Left | Medial Parietal | POS2 | 15 |
| Tract | Cingulum | Left | Medial Parietal | ProS | 121 |
| Tract | Cingulum | Right | Medial Parietal | 23d | 232 |
| Tract | Cingulum | Right | Medial Parietal | 7m | 230 |
| Tract | Cingulum | Right | Medial Parietal | DVT | 342 |
| Tract | Cingulum | Right | Medial Parietal | POS1 | 231 |
| Tract | Cingulum | Right | Medial Parietal | POS2 | 215 |
| Tract | Cingulum | Right | Medial Parietal | ProS | 321 |
| Tract | Cingulum | Right | Parietal | PCV | 227 |
| Tract | Cingulum | Left | PCC | 31a | 162 |
| Tract | Cingulum | Left | PCC | 31pd | 161 |
| Tract | Cingulum | Left | PCC | 31pv | 35 |
| Tract | Cingulum | Left | PCC | d23ab | 34 |
| Tract | Cingulum | Left | PCC | RSC | 14 |
| Tract | Cingulum | Left | PCC | v23ab | 33 |
| Tract | Cingulum | Right | PCC | 31a | 362 |
| Tract | Cingulum | Right | PCC | 31pd | 361 |
| Tract | Cingulum | Right | PCC | 31pv | 235 |
| Tract | Cingulum | Right | PCC | d23ab | 234 |
| Tract | Cingulum | Right | PCC | RSC | 214 |

TABLE 2-continued

Example mapping database

| Grouping | Level 1 | Level 2 | Level 3 | Parcellation | ID |
|---|---|---|---|---|---|
| Tract | Cingulum | Right | PCC | v23ab | 233 |
| Tract | Cingulum | Left | SMA | SCEF | 43 |
| Tract | Cingulum | Right | SMA | SCEF | 243 |
| Tract | Cingulum | Right | Superior Parietal | 23c | 238 |
| Tract | FAT | Left | DLPFC | s6-8 | 98 |
| Tract | FAT | Right | DLPFC | s6-8 | 298 |
| Tract | FAT | Left | Frontal | 44 | 74 |
| Tract | FAT | Left | Frontal | FOP4 | 108 |
| Tract | FAT | Right | Frontal | 44 | 274 |
| Tract | FAT | Right | Frontal | FOP4 | 308 |
| Tract | FAT | Left | Insula | MI | 109 |
| Tract | FAT | Right | Insula | MI | 309 |
| Tract | FAT | Left | Medial Frontal | 8BL | 70 |
| Tract | FAT | Right | Medial Frontal | 8BL | 270 |
| Tract | FAT | Left | SMA | 6ma | 44 |
| Tract | FAT | Left | SMA | SFL | 26 |
| Tract | FAT | Right | SMA | 6ma | 244 |
| Tract | FAT | Right | SMA | SFL | 226 |
| Tract | FAT | Left | Superior Opercula | FOP1 | 113 |
| Tract | FAT | Left | Superior Opercula | FOP3 | 114 |
| Tract | FAT | Right | Superior Opercula | FOP1 | 313 |
| Tract | FAT | Right | Superior Opercula | FOP3 | 314 |
| Tract | FAT | Left | Ventral Premotor | 6r | 78 |
| Tract | FAT | Right | Ventral Premotor | 6r | 278 |
| Tract | ILF | Left | Accessory Language | TE1a | 132 |
| Tract | ILF | Left | Accessory Language | TGv | 172 |
| Tract | ILF | Left | Bilateral | PeEc | 122 |
| Tract | ILF | Left | Bilateral | PHA2 | 155 |
| Tract | ILF | Left | Bilateral | PHA3 | 127 |
| Tract | ILF | Right | Bilateral | PeEc | 322 |
| Tract | ILF | Right | Bilateral | PHA2 | 355 |
| Tract | ILF | Right | Bilateral | PHA3 | 327 |
| Tract | ILF | Left | Dorsal Stream | V3A | 13 |
| Tract | ILF | Left | Dorsal Stream | V3B | 19 |
| Tract | ILF | Left | Dorsal Stream | V6A | 152 |
| Tract | ILF | Left | Dorsal Stream | V7 | 16 |
| Tract | ILF | Right | Dorsal Stream | V3A | 213 |
| Tract | ILF | Right | Dorsal Stream | V3B | 219 |
| Tract | ILF | Right | Dorsal Stream | V6A | 352 |
| Tract | ILF | Right | Dorsal Stream | V7 | 216 |
| Tract | ILF | Left | Inferior Parietal | PGp | 143 |
| Tract | ILF | Right | Inferior Parietal | PGp | 343 |
| Tract | ILF | Left | Lateral Parietal | TPOJ3 | 141 |
| Tract | ILF | Right | Lateral Parietal | TPOJ3 | 341 |
| Tract | ILF | Left | Lateral Stream | LO3 | 159 |
| Tract | ILF | Left | Lateral Stream | MST | 2 |
| Tract | ILF | Left | Lateral Stream | MT | 23 |
| Tract | ILF | Left | Lateral Stream | PH | 138 |
| Tract | ILF | Right | Lateral Stream | LO3 | 359 |
| Tract | ILF | Right | Lateral Stream | MST | 202 |
| Tract | ILF | Right | Lateral Stream | MT | 223 |
| Tract | ILF | Right | Lateral Stream | PH | 338 |
| Tract | ILF | Left | Medial | V1 | 1 |
| Tract | ILF | Left | Medial | V2 | 4 |
| Tract | ILF | Left | Medial | V3 | 5 |
| Tract | ILF | Left | Medial | V4 | 6 |
| Tract | ILF | Right | Medial | V1 | 201 |
| Tract | ILF | Right | Medial | V2 | 204 |
| Tract | ILF | Right | Medial | V3 | 205 |
| Tract | ILF | Right | Medial | V4 | 206 |
| Tract | ILF | Left | Parietal | 52 | 103 |
| Tract | ILF | Left | Supramarginal Gyrus | PI | 178 |
| Tract | ILF | Right | Supramarginal Gyrus | 52 | 303 |
| Tract | ILF | Right | Supramarginal Gyrus | PI | 378 |
| Tract | ILF | Left | Temporal | A5 | 125 |
| Tract | ILF | Left | Temporal | MBelt | 173 |
| Tract | ILF | Left | Temporal | STGa | 123 |
| Tract | ILF | Left | Temporal | TA2 | 107 |
| Tract | ILF | Left | Temporal | TF | 135 |
| Tract | ILF | Left | Temporal | TGd | 131 |
| Tract | ILF | Right | Temporal | A5 | 325 |
| Tract | ILF | Right | Temporal | MBelt | 373 |
| Tract | ILF | Right | Temporal | STGa | 323 |
| Tract | ILF | Right | Temporal | TA2 | 307 |
| Tract | ILF | Right | Temporal | TE1a | 332 |
| Tract | ILF | Right | Temporal | TF | 335 |

TABLE 2-continued

Example mapping database

| Grouping | Level 1 | Level 2 | Level 3 | Parcellation | ID |
|---|---|---|---|---|---|
| Tract | ILF | Right | Temporal | TGd | 331 |
| Tract | ILF | Right | Temporal | TGv | 372 |
| Tract | ILF | Left | Ventral Stream | FFC | 18 |
| Tract | ILF | Left | Ventral Stream | V8 | 7 |
| Tract | ILF | Left | Ventral Stream | VMV1 | 153 |
| Tract | ILF | Left | Ventral Stream | VMV2 | 160 |
| Tract | ILF | Left | Ventral Stream | VMV3 | 154 |
| Tract | ILF | Left | Ventral Stream | VVC | 163 |
| Tract | ILF | Right | Ventral Stream | FFC | 218 |
| Tract | ILF | Right | Ventral Stream | V8 | 207 |
| Tract | ILF | Right | Ventral Stream | VMV1 | 353 |
| Tract | ILF | Right | Ventral Stream | VMV2 | 360 |
| Tract | ILF | Right | Ventral Stream | VMV3 | 354 |
| Tract | ILF | Right | Ventral Stream | VVC | 363 |
| Tract | IFOF | Left | DLPFC | 9a | 87 |
| Tract | IFOF | Left | DLPFC | 9p | 71 |
| Tract | IFOF | Right | DLPFC | 47l | 276 |
| Tract | IFOF | Right | DLPFC | 9a | 287 |
| Tract | IFOF | Right | DLPFC | 9p | 271 |
| Tract | IFOF | Left | Dorsal Premotor | 6a | 96 |
| Tract | IFOF | Right | Dorsal Premotor | 6a | 296 |
| Tract | IFOF | Left | Dorsal Stream | IPS1 | 17 |
| Tract | IFOF | Left | Dorsal Stream | V3A | 13 |
| Tract | IFOF | Left | Dorsal Stream | V6 | 3 |
| Tract | IFOF | Left | Dorsal Stream | V6A | 152 |
| Tract | IFOF | Left | Dorsal Stream | V7 | 16 |
| Tract | IFOF | Right | Dorsal Stream | IPS1 | 217 |
| Tract | IFOF | Right | Dorsal Stream | V3A | 213 |
| Tract | IFOF | Right | Dorsal Stream | V6 | 203 |
| Tract | IFOF | Right | Dorsal Stream | V6A | 352 |
| Tract | IFOF | Right | Dorsal Stream | V7 | 216 |
| Tract | IFOF | Left | Frontal | 45 | 75 |
| Tract | IFOF | Left | Frontal | 47l | 76 |
| Tract | IFOF | Left | Frontal | a47r | 77 |
| Tract | IFOF | Right | Frontal | a47r | 277 |
| Tract | IFOF | Left | Frontopolar | 10d | 72 |
| Tract | IFOF | Left | Frontopolar | 10pp | 90 |
| Tract | IFOF | Left | Frontopolar | a10p | 89 |
| Tract | IFOF | Left | Frontopolar | p10p | 170 |
| Tract | IFOF | Right | Frontopolar | 10d | 272 |
| Tract | IFOF | Right | Frontopolar | 10pp | 290 |
| Tract | IFOF | Right | Frontopolar | a10p | 289 |
| Tract | IFOF | Right | Frontopolar | p10p | 370 |
| Tract | IFOF | Left | Insula | FOP5 | 169 |
| Tract | IFOF | Right | Insula | FOP5 | 369 |
| Tract | IFOF | Left | Medial | V1 | 1 |
| Tract | IFOF | Left | Medial | V2 | 4 |
| Tract | IFOF | Left | Medial | V3 | 5 |
| Tract | IFOF | Left | Medial | V4 | 6 |
| Tract | IFOF | Right | Medial | V1 | 201 |
| Tract | IFOF | Right | Medial | V2 | 204 |
| Tract | IFOF | Right | Medial | V3 | 205 |
| Tract | IFOF | Right | Medial | V4 | 206 |
| Tract | IFOF | Left | Medial Frontal | 8BL | 70 |
| Tract | IFOF | Left | Medial Frontal | 9m | 69 |
| Tract | IFOF | Right | Medial Frontal | 8BL | 270 |
| Tract | IFOF | Right | Medial Frontal | 9m | 269 |
| Tract | IFOF | Left | Orbitofrontal | 11l | 91 |
| Tract | IFOF | Left | Orbitofrontal | 47s | 94 |
| Tract | IFOF | Left | Orbitofrontal | OFC | 93 |
| Tract | IFOF | Right | Orbitofrontal | 11l | 291 |
| Tract | IFOF | Right | Orbitofrontal | 47s | 294 |
| Tract | IFOF | Right | Orbitofrontal | OFC | 293 |
| Tract | IFOF | Left | Parietal | 7AL | 42 |
| Tract | IFOF | Left | Parietal | 7PC | 47 |
| Tract | IFOF | Left | Parietal | MIP | 50 |
| Tract | IFOF | Right | Parietal | 7Am | 245 |
| Tract | IFOF | Right | Parietal | 7PC | 247 |
| Tract | IFOF | Right | Parietal | MIP | 250 |
| Tract | IFOF | Left | SMA | 6ma | 44 |
| Tract | IFOF | Left | SMA | SFL | 26 |
| Tract | IFOF | Right | SMA | 6ma | 244 |
| Tract | IFOF | Right | SMA | SFL | 226 |
| Tract | IFOF | Left | Superior Parietal | 7Am | 45 |
| Tract | IFOF | Left | Superior Parietal | 7PL | 46 |
| Tract | IFOF | Right | Superior Parietal | 7AL | 242 |

TABLE 2-continued

Example mapping database

| Grouping | Level 1 | Level 2 | Level 3 | Parcellation | ID |
|---|---|---|---|---|---|
| Tract | IFOF | Right | Superior Parietal | 7PL | 246 |
| Tract | IFOF | Left | Ventral Stream | VMV2 | 160 |
| Tract | IFOF | Right | Ventral Stream | VMV2 | 360 |
| Tract | IFOF | Right | | 45 | 275 |
| Tract | MdLF | Left | Accessory Language | STSda | 128 |
| Tract | MdLF | Left | Accessory Language | STSva | 176 |
| Tract | MdLF | Left | Accessory Language | TE1a | 132 |
| Tract | MdLF | Left | Dorsal Stream | IPS1 | 17 |
| Tract | MdLF | Left | Dorsal Stream | V3A | 13 |
| Tract | MdLF | Left | Dorsal Stream | V3B | 19 |
| Tract | MdLF | Left | Dorsal Stream | V6 | 3 |
| Tract | MdLF | Left | Dorsal Stream | V6A | 152 |
| Tract | MdLF | Left | Dorsal Stream | V7 | 16 |
| Tract | MdLF | Right | Dorsal Stream | IPS1 | 217 |
| Tract | MdLF | Right | Dorsal Stream | V3A | 213 |
| Tract | MdLF | Right | Dorsal Stream | V3B | 219 |
| Tract | MdLF | Right | Dorsal Stream | V6 | 203 |
| Tract | MdLF | Right | Dorsal Stream | V6A | 352 |
| Tract | MdLF | Right | Dorsal Stream | V7 | 216 |
| Tract | MdLF | Left | Insula Proper | PoI1 | 167 |
| Tract | MdLF | Left | Insula Proper | PoI2 | 106 |
| Tract | MdLF | Right | Insula Proper | PoI1 | 367 |
| Tract | MdLF | Right | Insula Proper | PoI2 | 306 |
| Tract | MdLF | Left | IPS | IP0 | 146 |
| Tract | MdLF | Right | IPS | IP0 | 346 |
| Tract | MdLF | Left | Lateral Parietal | IP1 | 145 |
| Tract | MdLF | Right | Lateral Parietal | IP1 | 345 |
| Tract | MdLF | Left | Lateral Stream | V3CD | 158 |
| Tract | MdLF | Right | Lateral Stream | V3CD | 358 |
| Tract | MdLF | Left | Medial | V1 | 1 |
| Tract | MdLF | Left | Medial | V2 | 4 |
| Tract | MdLF | Left | Medial | V3 | 5 |
| Tract | MdLF | Left | Medial | V4 | 6 |
| Tract | MdLF | Right | Medial | V1 | 201 |
| Tract | MdLF | Right | Medial | V2 | 204 |
| Tract | MdLF | Right | Medial | V3 | 205 |
| Tract | MdLF | Right | Medial | V4 | 206 |
| Tract | MdLF | Left | Parietal | LIPd | 95 |
| Tract | MdLF | Left | Parietal | LIPv | 48 |
| Tract | MdLF | Left | Parietal | MIP | 50 |
| Tract | MdLF | Left | Parietal | VIP | 49 |
| Tract | MdLF | Right | Parietal | LIPd | 295 |
| Tract | MdLF | Right | Parietal | LIPv | 248 |
| Tract | MdLF | Right | Parietal | MIP | 250 |
| Tract | MdLF | Right | Parietal | VIP | 249 |
| Tract | MdLF | Left | Superior Parietal | 7PL | 46 |
| Tract | MdLF | Right | Superior Parietal | 7PL | 246 |
| Tract | MdLF | Left | Supramarginal Gyrus | PI | 178 |
| Tract | MdLF | Right | Supramarginal Gyrus | PI | 378 |
| Tract | MdLF | Left | Temporal | A1 | 24 |
| Tract | MdLF | Left | Temporal | A4 | 175 |
| Tract | MdLF | Left | Temporal | A5 | 125 |
| Tract | MdLF | Left | Temporal | MBelt | 173 |
| Tract | MdLF | Left | Temporal | PBelt | 124 |
| Tract | MdLF | Left | Temporal | STGa | 123 |
| Tract | MdLF | Left | Temporal | STSdp | 129 |
| Tract | MdLF | Left | Temporal | TGd | 131 |
| Tract | MdLF | Right | Temporal | A1 | 224 |
| Tract | MdLF | Right | Temporal | A4 | 375 |
| Tract | MdLF | Right | Temporal | A5 | 325 |
| Tract | MdLF | Right | Temporal | MBelt | 373 |
| Tract | MdLF | Right | Temporal | PBelt | 324 |
| Tract | MdLF | Right | Temporal | STGa | 323 |
| Tract | MdLF | Right | Temporal | STSda | 328 |
| Tract | MdLF | Right | Temporal | STSdp | 329 |
| Tract | MdLF | Right | Temporal | STSva | 376 |
| Tract | MdLF | Right | Temporal | TE1a | 332 |
| Tract | MdLF | Right | Temporal | TGd | 331 |
| Tract | SLF/AF | Left | Accessory Language | STSda | 128 |
| Tract | SLF/AF | Left | Accessory Language | STSva | 176 |
| Tract | SLF/AF | Left | Accessory Language | TE1a | 132 |
| Tract | SLF/AF | Left | DLPFC | IFJp | 80 |
| Tract | SLF/AF | Left | DLPFC | PEF | 11 |
| Tract | SLF/AF | Right | DLPFC | IFJa | 279 |
| Tract | SLF/AF | Right | DLPFC | IFJp | 280 |
| Tract | SLF/AF | Right | DLPFC | PEF | 211 |

TABLE 2-continued

Example mapping database

| Grouping | Level 1 | Level 2 | Level 3 | Parcellation | ID |
|---|---|---|---|---|---|
| Tract | SLF/AF | Left | Dorsal Premotor | 6a | 96 |
| Tract | SLF/AF | Right | Dorsal Premotor | 6a | 296 |
| Tract | SLF/AF | Left | Frontal | 44 | 74 |
| Tract | SLF/AF | Left | Frontal | 45 | 75 |
| Tract | SLF/AF | Left | Frontal | 46 | 84 |
| Tract | SLF/AF | Left | Frontal | 55b | 12 |
| Tract | SLF/AF | Left | Frontal | 8Av | 67 |
| Tract | SLF/AF | Left | Frontal | 8C | 73 |
| Tract | SLF/AF | Left | Frontal | FEF | 10 |
| Tract | SLF/AF | Left | Frontal | FOP4 | 108 |
| Tract | SLF/AF | Left | Frontal | IFJa | 79 |
| Tract | SLF/AF | Left | Frontal | IFSa | 82 |
| Tract | SLF/AF | Left | Frontal | IFSp | 81 |
| Tract | SLF/AF | Left | Frontal | p9-46v | 83 |
| Tract | SLF/AF | Right | Frontal | 44 | 274 |
| Tract | SLF/AF | Right | Frontal | 46 | 284 |
| Tract | SLF/AF | Right | Frontal | 8Av | 267 |
| Tract | SLF/AF | Right | Frontal | 8C | 273 |
| Tract | SLF/AF | Right | Frontal | FEF | 210 |
| Tract | SLF/AF | Right | Frontal | FOP4 | 308 |
| Tract | SLF/AF | Right | Frontal | IFSa | 282 |
| Tract | SLF/AF | Right | Frontal | IFSp | 281 |
| Tract | SLF/AF | Right | Frontal | p9-46v | 283 |
| Tract | SLF/AF | Left | Inferior Parietal | TPOJ2 | 140 |
| Tract | SLF/AF | Left | Insula | FOP5 | 169 |
| Tract | SLF/AF | Left | Insula | MI | 109 |
| Tract | SLF/AF | Right | Insula | FOP5 | 369 |
| Tract | SLF/AF | Right | Insula | MI | 309 |
| Tract | SLF/AF | Left | IPS | IP2 | 144 |
| Tract | SLF/AF | Right | IPS | IP2 | 344 |
| Tract | SLF/AF | Left | Lateral Parietal | IP1 | 145 |
| Tract | SLF/AF | Left | Lateral Parietal | PGs | 151 |
| Tract | SLF/AF | Right | Lateral Parietal | IP1 | 345 |
| Tract | SLF/AF | Right | Lateral Parietal | PGs | 351 |
| Tract | SLF/AF | Left | Lateral Stream | FST | 157 |
| Tract | SLF/AF | Left | Lateral Stream | PH | 138 |
| Tract | SLF/AF | Right | Lateral Stream | FST | 357 |
| Tract | SLF/AF | Right | Lateral Stream | PH | 338 |
| Tract | SLF/AF | Left | Medial Frontal | 8BM | 63 |
| Tract | SLF/AF | Right | Medial Frontal | 8BM | 263 |
| Tract | SLF/AF | Left | Parietal | 7PC | 47 |
| Tract | SLF/AF | Left | Parietal | AIP | 117 |
| Tract | SLF/AF | Left | Parietal | LIPd | 95 |
| Tract | SLF/AF | Left | Parietal | MIP | 50 |
| Tract | SLF/AF | Left | Parietal | PF | 148 |
| Tract | SLF/AF | Left | Parietal | PFcm | 105 |
| Tract | SLF/AF | Left | Parietal | PFm | 149 |
| Tract | SLF/AF | Left | Parietal | PFt | 116 |
| Tract | SLF/AF | Left | Parietal | PSL | 25 |
| Tract | SLF/AF | Right | Parietal | 7PC | 247 |
| Tract | SLF/AF | Right | Parietal | AIP | 317 |
| Tract | SLF/AF | Right | Parietal | LIPd | 295 |
| Tract | SLF/AF | Right | Parietal | MIP | 250 |
| Tract | SLF/AF | Right | Parietal | PF | 348 |
| Tract | SLF/AF | Right | Parietal | PFcm | 305 |
| Tract | SLF/AF | Right | Parietal | PFm | 349 |
| Tract | SLF/AF | Right | Parietal | PFt | 316 |
| Tract | SLF/AF | Right | Parietal | PSL | 225 |
| Tract | SLF/AF | Right | Parietal | TPOJ2 | 340 |
| Tract | SLF/AF | Left | Primary | 1 | 51 |
| Tract | SLF/AF | Left | Primary | 2 | 52 |
| Tract | SLF/AF | Left | Primary | 4 | 8 |
| Tract | SLF/AF | Left | Primary | 3a | 53 |
| Tract | SLF/AF | Left | Primary | 3b | 9 |
| Tract | SLF/AF | Right | Primary | 1 | 251 |
| Tract | SLF/AF | Right | Primary | 2 | 252 |
| Tract | SLF/AF | Right | Primary | 4 | 208 |
| Tract | SLF/AF | Right | Primary | 3a | 253 |
| Tract | SLF/AF | Right | Primary | 3b | 209 |
| Tract | SLF/AF | Left | Superior Opercula | 43 | 99 |
| Tract | SLF/AF | Left | Superior Opercula | FOP1 | 113 |
| Tract | SLF/AF | Left | Superior Opercula | FOP2 | 115 |
| Tract | SLF/AF | Left | Superior Opercula | FOP3 | 114 |
| Tract | SLF/AF | Left | Superior Opercula | OP4 | 100 |
| Tract | SLF/AF | Right | Superior Opercula | 43 | 299 |
| Tract | SLF/AF | Right | Superior Opercula | FOP1 | 313 |

TABLE 2-continued

Example mapping database

| Grouping | Level 1 | Level 2 | Level 3 | Parcellation | ID |
|---|---|---|---|---|---|
| Tract | SLF/AF | Right | Superior Opercula | FOP2 | 315 |
| Tract | SLF/AF | Right | Superior Opercula | FOP3 | 314 |
| Tract | SLF/AF | Right | Superior Opercula | OP4 | 300 |
| Tract | SLF/AF | Left | Supramarginal Gyrus | STV | 28 |
| Tract | SLF/AF | Right | Supramarginal Gyrus | STV | 228 |
| Tract | SLF/AF | Left | Temporal | A1 | 24 |
| Tract | SLF/AF | Left | Temporal | A4 | 175 |
| Tract | SLF/AF | Left | Temporal | A5 | 125 |
| Tract | SLF/AF | Left | Temporal | LBelt | 174 |
| Tract | SLF/AF | Left | Temporal | PBelt | 124 |
| Tract | SLF/AF | Left | Temporal | PHT | 137 |
| Tract | SLF/AF | Left | Temporal | RI | 104 |
| Tract | SLF/AF | Left | Temporal | STSdp | 129 |
| Tract | SLF/AF | Left | Temporal | STSvp | 130 |
| Tract | SLF/AF | Left | Temporal | TE1m | 177 |
| Tract | SLF/AF | Left | Temporal | TE1p | 133 |
| Tract | SLF/AF | Left | Temporal | TE2a | 134 |
| Tract | SLF/AF | Left | Temporal | TE2p | 136 |
| Tract | SLF/AF | Left | Temporal | TF | 135 |
| Tract | SLF/AF | Left | Temporal | TGd | 131 |
| Tract | SLF/AF | Left | Temporal | TPOJ1 | 139 |
| Tract | SLF/AF | Right | Temporal | A1 | 224 |
| Tract | SLF/AF | Right | Temporal | A4 | 375 |
| Tract | SLF/AF | Right | Temporal | A5 | 325 |
| Tract | SLF/AF | Right | Temporal | LBelt | 374 |
| Tract | SLF/AF | Right | Temporal | PBelt | 324 |
| Tract | SLF/AF | Right | Temporal | PHT | 337 |
| Tract | SLF/AF | Right | Temporal | RI | 304 |
| Tract | SLF/AF | Right | Temporal | STSda | 328 |
| Tract | SLF/AF | Right | Temporal | STSdp | 329 |
| Tract | SLF/AF | Right | Temporal | STSva | 376 |
| Tract | SLF/AF | Right | Temporal | STSvp | 330 |
| Tract | SLF/AF | Right | Temporal | TE1a | 332 |
| Tract | SLF/AF | Right | Temporal | TE1m | 377 |
| Tract | SLF/AF | Right | Temporal | TE1p | 333 |
| Tract | SLF/AF | Right | Temporal | TE2a | 334 |
| Tract | SLF/AF | Right | Temporal | TE2p | 336 |
| Tract | SLF/AF | Right | Temporal | TF | 335 |
| Tract | SLF/AF | Right | Temporal | TGd | 331 |
| Tract | SLF/AF | Right | Temporal | TPOJ1 | 339 |
| Tract | SLF/AF | Left | Ventral Premotor | 6r | 78 |
| Tract | SLF/AF | Left | Ventral Premotor | 6v | 56 |
| Tract | SLF/AF | Right | Ventral Premotor | 6r | 278 |
| Tract | SLF/AF | Right | Ventral Premotor | 6v | 256 |
| Tract | SLF/AF | Right | | 45 | 275 |
| Tract | SLF/AF | Right | | 55b | 212 |
| Tract | UF | Right | DLPFC | 47l | 276 |
| Tract | UF | Left | Frontal | 44 | 74 |
| Tract | UF | Left | Frontal | 45 | 75 |
| Tract | UF | Left | Frontal | 47l | 76 |
| Tract | UF | Left | Frontal | FOP4 | 108 |
| Tract | UF | Right | Frontal | 44 | 274 |
| Tract | UF | Right | Frontal | FOP4 | 308 |
| Tract | UF | Left | Insula | FOP5 | 169 |
| Tract | UF | Right | Insula | FOP5 | 369 |
| Tract | UF | Left | Orbitofrontal | 47s | 94 |
| Tract | UF | Left | Orbitofrontal | OFC | 93 |
| Tract | UF | Left | Orbitofrontal | pOFC | 166 |
| Tract | UF | Right | Orbitofrontal | 47s | 294 |
| Tract | UF | Right | Orbitofrontal | OFC | 293 |
| Tract | UF | Right | Orbitofrontal | pOFC | 366 |
| Tract | UF | Left | Temporal | STGa | 123 |
| Tract | UF | Left | Temporal | TGd | 131 |
| Tract | UF | Right | Temporal | STGa | 323 |
| Tract | UF | Right | Temporal | TGd | 331 |
| Tract | UF | Right | | 45 | 275 |
| Tract | VOF | Left | Dorsal Stream | V3A | 13 |
| Tract | VOF | Left | Dorsal Stream | V3B | 19 |
| Tract | VOF | Left | Dorsal Stream | V7 | 16 |
| Tract | VOF | Right | Dorsal Stream | V3A | 213 |
| Tract | VOF | Right | Dorsal Stream | V3B | 219 |
| Tract | VOF | Right | Dorsal Stream | V7 | 216 |
| Tract | VOF | Left | Lateral Stream | V3CD | 158 |
| Tract | VOF | Right | Lateral Stream | V3CD | 358 |
| Tract | VOF | Left | Medial | V2 | 4 |
| Tract | VOF | Left | Medial | V3 | 5 |

TABLE 2-continued

Example mapping database

| Grouping | Level 1 | Level 2 | Level 3 | Parcellation | ID |
|---|---|---|---|---|---|
| Tract | VOF | Right | Medial | V2 | 204 |
| Tract | VOF | Right | Medial | V3 | 205 |
| Tract | VOF | Left | Ventral Stream | PIT | 22 |
| Tract | VOF | Left | Ventral Stream | V8 | 7 |
| Tract | VOF | Left | Ventral Stream | VMV1 | 153 |
| Tract | VOF | Left | Ventral Stream | VMV2 | 160 |
| Tract | VOF | Left | Ventral Stream | VMV3 | 154 |
| Tract | VOF | Left | Ventral Stream | VVC | 163 |
| Tract | VOF | Right | Ventral Stream | PIT | 222 |
| Tract | VOF | Right | Ventral Stream | V8 | 207 |
| Tract | VOF | Right | Ventral Stream | VMV1 | 353 |
| Tract | VOF | Right | Ventral Stream | VMV2 | 360 |
| Tract | VOF | Right | Ventral Stream | VMV3 | 354 |
| Tract | VOF | Right | Ventral Stream | VVC | 363 |
| Region | DLPFC | Left | | 9-46d | 86 |
| Region | DLPFC | Left | | 9a | 87 |
| Region | DLPFC | Left | | 9p | 71 |
| Region | DLPFC | Left | | a9-46v | 85 |
| Region | DLPFC | Left | | i6-8 | 97 |
| Region | DLPFC | Left | | IFJp | 80 |
| Region | DLPFC | Left | | PEF | 11 |
| Region | DLPFC | Left | | s6-8 | 98 |
| Region | DLPFC | Right | | 47l | 276 |
| Region | DLPFC | Right | | 9-46d | 286 |
| Region | DLPFC | Right | | 9a | 287 |
| Region | DLPFC | Right | | 9p | 271 |
| Region | DLPFC | Right | | a9-46v | 285 |
| Region | DLPFC | Right | | i6-8 | 297 |
| Region | DLPFC | Right | | IFJa | 279 |
| Region | DLPFC | Right | | IFJp | 280 |
| Region | DLPFC | Right | | PEF | 211 |
| Region | DLPFC | Right | | s6-8 | 298 |
| Region | Frontopolar | Left | | 10d | 72 |
| Region | Frontopolar | Left | | 10pp | 90 |
| Region | Frontopolar | Left | | a10p | 89 |
| Region | Frontopolar | Left | | p10p | 170 |
| Region | Frontopolar | Right | | 10d | 272 |
| Region | Frontopolar | Right | | 10pp | 290 |
| Region | Frontopolar | Right | | a10p | 289 |
| Region | Frontopolar | Right | | p10p | 370 |
| Region | Inferior Parietal | Left | | PGp | 143 |
| Region | Inferior Parietal | Left | | TPOJ2 | 140 |
| Region | Inferior Parietal | Right | | PGp | 343 |
| Region | Insula Proper | Left | | AAIC | 112 |
| Region | Insula Proper | Left | | Ig | 168 |
| Region | Insula Proper | Left | | Pir | 110 |
| Region | Insula Proper | Left | | PoI1 | 167 |
| Region | Insula Proper | Left | | PoI2 | 106 |
| Region | Insula Proper | Right | | AAIC | 312 |
| Region | Insula Proper | Right | | Ig | 368 |
| Region | Insula Proper | Right | | Pir | 310 |
| Region | Insula Proper | Right | | PoI1 | 367 |
| Region | Insula Proper | Right | | PoI2 | 306 |
| Region | IPS | Left | | IP0 | 146 |
| Region | IPS | Left | | IP2 | 144 |
| Region | IPS | Right | | IP0 | 346 |
| Region | IPS | Right | | IP2 | 344 |
| Region | Medial Frontal | Left | | 25 | 164 |
| Region | Medial Frontal | Left | | 10v | 88 |
| Region | Medial Frontal | Left | | 33pr | 58 |
| Region | Medial Frontal | Left | | 8BL | 70 |
| Region | Medial Frontal | Left | | 8BM | 63 |
| Region | Medial Frontal | Left | | 9m | 69 |
| Region | Medial Frontal | Left | | a32pr | 179 |
| Region | Medial Frontal | Left | | d32 | 62 |
| Region | Medial Frontal | Left | | p24 | 180 |
| Region | Medial Frontal | Left | | p24pr | 57 |
| Region | Medial Frontal | Right | | 25 | 364 |
| Region | Medial Frontal | Right | | 10v | 288 |
| Region | Medial Frontal | Right | | 33pr | 258 |
| Region | Medial Frontal | Right | | 8BL | 270 |
| Region | Medial Frontal | Right | | 8BM | 263 |
| Region | Medial Frontal | Right | | 9m | 269 |
| Region | Medial Frontal | Right | | a32pr | 379 |
| Region | Medial Frontal | Right | | d32 | 262 |
| Region | Medial Frontal | Right | | p24 | 380 |

TABLE 2-continued

Example mapping database

| Grouping | Level 1 | Level 2 | Level 3 | Parcellation | ID |
| --- | --- | --- | --- | --- | --- |
| Region | Medial Frontal | Right | | p24pr | 257 |
| Region | Medial Parietal | Left | | 23c | 38 |
| Region | Medial Parietal | Left | | 23d | 32 |
| Region | Medial Parietal | Left | | 7m | 30 |
| Region | Medial Parietal | Left | | DVT | 142 |
| Region | Medial Parietal | Left | | PCV | 27 |
| Region | Medial Parietal | Left | | POS1 | 31 |
| Region | Medial Parietal | Left | | POS2 | 15 |
| Region | Medial Parietal | Left | | ProS | 121 |
| Region | Medial Parietal | Right | | 23d | 232 |
| Region | Medial Parietal | Right | | 7m | 230 |
| Region | Medial Parietal | Right | | DVT | 342 |
| Region | Medial Parietal | Right | | POS1 | 231 |
| Region | Medial Parietal | Right | | POS2 | 215 |
| Region | Medial Parietal | Right | | ProS | 321 |
| Region | Orbitofrontal | Left | | 11l | 91 |
| Region | Orbitofrontal | Left | | 13l | 92 |
| Region | Orbitofrontal | Left | | 47m | 66 |
| Region | Orbitofrontal | Left | | 47s | 94 |
| Region | Orbitofrontal | Left | | OFC | 93 |
| Region | Orbitofrontal | Left | | pOFC | 166 |
| Region | Orbitofrontal | Right | | 11l | 291 |
| Region | Orbitofrontal | Right | | 13l | 292 |
| Region | Orbitofrontal | Right | | 47m | 266 |
| Region | Orbitofrontal | Right | | 47s | 294 |
| Region | Orbitofrontal | Right | | OFC | 293 |
| Region | Orbitofrontal | Right | | pOFC | 366 |
| Region | Superior Opercula | Left | | 43 | 99 |
| Region | Superior Opercula | Left | | FOP1 | 113 |
| Region | Superior Opercula | Left | | FOP2 | 115 |
| Region | Superior Opercula | Left | | FOP3 | 114 |
| Region | Superior Opercula | Left | | OP1 | 101 |
| Region | Superior Opercula | Left | | OP2-3 | 102 |
| Region | Superior Opercula | Left | | OP4 | 100 |
| Region | Superior Opercula | Right | | 43 | 299 |
| Region | Superior Opercula | Right | | FOP1 | 313 |
| Region | Superior Opercula | Right | | FOP2 | 315 |
| Region | Superior Opercula | Right | | FOP3 | 314 |
| Region | Superior Opercula | Right | | OP1 | 301 |
| Region | Superior Opercula | Right | | OP2-3 | 302 |
| Region | Superior Opercula | Right | | OP4 | 300 |
| Region | Superior Opercula | Right | | PFop | 347 |
| Region | Superior Parietal | Left | | 5L | 39 |
| Region | Superior Parietal | Left | | 5m | 36 |
| Region | Superior Parietal | Left | | 5mv | 37 |
| Region | Superior Parietal | Left | | 7Am | 45 |
| Region | Superior Parietal | Left | | 7PL | 46 |
| Region | Superior Parietal | Left | | 7Pm | 29 |
| Region | Superior Parietal | Right | | 23c | 238 |
| Region | Superior Parietal | Right | | 5L | 239 |
| Region | Superior Parietal | Right | | 5m | 236 |
| Region | Superior Parietal | Right | | 5mv | 237 |
| Region | Superior Parietal | Right | | 7AL | 242 |
| Region | Superior Parietal | Right | | 7PL | 246 |
| Region | Supramarginal Gyrus | Left | | PI | 178 |
| Region | Supramarginal Gyrus | Left | | STV | 28 |
| Region | Supramarginal Gyrus | Right | | 52 | 303 |
| Region | Supramarginal Gyrus | Right | | PI | 378 |
| Region | Supramarginal Gyrus | Right | | STV | 228 |
| Region | Temporal | Left | | STGa | 123 |
| Region | Temporal | Left | | TA2 | 107 |
| Region | Temporal | Left | | TE1m | 177 |
| Region | Temporal | Left | | TE2a | 134 |
| Region | Temporal | Left | | TE2p | 136 |
| Region | Temporal | Left | | TF | 135 |
| Region | Temporal | Left | | TGd | 131 |
| Region | Temporal | Right | | PHT | 337 |
| Region | Temporal | Right | | STGa | 323 |
| Region | Temporal | Right | | STSda | 328 |
| Region | Temporal | Right | | STSva | 376 |
| Region | Temporal | Right | | STSvp | 330 |
| Region | Temporal | Right | | TA2 | 307 |
| Region | Temporal | Right | | TE1a | 332 |
| Region | Temporal | Right | | TE1m | 377 |
| Region | Temporal | Right | | TE1p | 333 |
| Region | Temporal | Right | | TE2a | 334 |

TABLE 2-continued

Example mapping database

| Grouping | Level 1 | Level 2 | Level 3 | Parcellation | ID |
|---|---|---|---|---|---|
| Region | Temporal | Right | | TE2p | 336 |
| Region | Temporal | Right | | TF | 335 |
| Region | Temporal | Right | | TGd | 331 |
| Region | Temporal | Right | | TGv | 372 |

The invention claimed is:

1. A method comprising:
receiving a first user input to expand a currently available menu option, the currently available menu option for selecting a grouping network of a subject brain;
determining updated menu data for a menu based on the first user input;
providing the updated menu data for display to a user including at least one grouping option for selecting the grouping network of the subject brain and at least a level one option for selecting a level one network of the subject brain where the grouping network includes the level one network;
receiving a selection of a network of the subject brain to specify a selected network;
determining, based on an MRI image of the subject brain and one or more identifiers associated with the selected network, parcellations of the selected network of the subject brain to produce determined parcellations;
determining, using three-dimensional coordinates associated with each determined parcellation, corresponding tracts in a diffusion tensor image of the brain to produce determined tracts, wherein determining corresponding tracts in a diffusion tensor image of the brain to produce determined tracts comprises:
receiving a tract selection mode indication to select only tracts that: a) begin in one of the determined parcellations and b) end in another one of the determined parcellations; and
responsive to the tract selection mode indication, determining corresponding tracts in a diffusion tensor image of the brain to produce determined tracts that only a) begin in one of the determined parcellations and b) end in another one of the determined parcellations; and
generating a graphical representation of the selected network, the graphical representation including at least one of (i) one or more surfaces representing the one or more determined parcellations, each surface generated using the coordinates, and (ii) the determined tracts.

2. The method according to claim 1, wherein each of the one or more parcellations is determined based on a database associating three-dimensional locations in the subject brain with a parcellation identifier and wherein the graphical representation including both (i) one or more surfaces representing the one or more determined parcellations, each surface generated using the coordinates, and (ii) the determined tracts.

3. The method according to claim 1, wherein each of the one or more parcellations is determined based on a parcellation name and a corresponding region of the subject brain.

4. The method of claim 1, wherein the determined tracts comprise all tracts intersecting regions associated with the determined one or more parcellations.

5. The method according to claim 1, wherein determining the one or more parcellations comprises generating a three-dimensional model of the brain from the MRI image, each voxel of the MRI image having an associated identifier.

6. The method according to claim 1, further comprising generating a surface model, the surface model associating a set of RGB values with a coordinate of each voxel, the RGB values reflecting a parcellation of the subject brain, and wherein the one or more surfaces are generated using the surface model.

7. The method according to claim 1, wherein a mapping database associates the identifiers such that each of a plurality of parcellation identifiers matches a mesh identifier in the corresponding three-dimensional location.

8. The method according to claim 1, wherein the three-dimensional coordinates associated with each parcellation are determined based on voxel positions in the MRI data.

9. The method according to claim 1, wherein the corresponding tracts include subsets of tracts of the subject human brain.

10. A non-transitory computer readable medium having a computer program stored thereon to implement a method, the program comprising:
code for receiving a first user input to expand a currently available menu option, the currently available menu option for selecting a grouping network of a subject brain;
code for determining updated menu data for a menu based on the first user input;
code for providing the updated menu data for display to a user—including at least one grouping option for selecting the grouping network of the subject brain and at least a level one option for selecting a level one network of the subject brain where the grouping network includes the level one network;
code for receiving a selection of a network of the subject brain to specify a selected network;
code for determining, based on an MRI image of the subject brain and one or more identifiers associated with the selected network, parcellations of the selected network of the subject brain to produce determined parcellations;
code for determining, using three-dimensional coordinates associated with each determined parcellation, corresponding tracts in a diffusion tensor image of the brain to produce determined tracts, wherein determining corresponding tracts in a diffusion tensor image of the brain to produce determined tracts comprises:
receiving a tract selection mode indication to select only tracts that: a) begin in one of the determined parcellations and b) end in another one of the determined parcellations; and
responsive to the tract selection mode indication, determining corresponding tracts in a diffusion tensor image of the brain to produce determined tracts that only a) begin in one of the determined parcellations and b) end in another one of the determined parcellations; and code for generating a graphical representation of the selected network, the graphical representation including at least one of (i) one or more surfaces representing the one or more determined parcellations, each surface generated using the coordinates, and (ii) the determined tracts.

11. A system comprising
one or more computers and one or more storage devices on which are stored instructions that are operable, when executed by the one or more computers, to cause the one or more computers to perform operations comprising:
receiving a first user input to expand a currently available menu option, the currently available menu option for selecting a grouping network of a brain;
determining updated menu data for a menu based on the first user input;
providing the updated menu data for display to a user including at least one grouping option for selecting the grouping network of the subject brain and at least a level one option for selecting a level one network of the subject brain where the grouping network includes the level one network;
receiving a selection of a network of the subject brain to specify a selected network;
determining, based on an MRI image of the subject brain and one or more identifiers associated with the selected network, parcellations of the selected network of the subject brain to produce determined parcellations;
determining, using three-dimensional coordinates associated with each determined parcellation, corresponding tracts in a diffusion tensor image of the brain to produce determined tracts, wherein determining corresponding tracts in a diffusion tensor image of the brain to produce determined tracts comprises:
receiving a tract selection mode indication to select only tracts that: a) begin in one of the determined parcellations and b) end in another one of the determined parcellations; and
responsive to the tract selection mode indication, determining corresponding tracts in a diffusion tensor image of the brain to produce determined tracts that only a) begin in one of the determined parcellations and b) end in another one of the determined parcellations; and
generating a graphical representation of the selected network, the graphical representation including at least one of (i) one or more surfaces representing the one or more determined parcellations, each surface generated using the coordinates, and (ii) the determined tracts.

12. The system according to claim 11, wherein each of the one or more parcellations is determined based on a database associating three-dimensional locations in the subject brain with a parcellation identifier and wherein the graphical representation including both (i) one or more surfaces representing the one or more determined parcellations, each surface generated using the coordinates, and (ii) the determined tracts.

13. The system according to claim 11, wherein each of the one or more parcellations is determined based on a parcellation name and a corresponding region of the subject brain.

14. The system of claim 11, wherein the determined tracts comprise all tracts intersecting regions associated with the determined one or more parcellations.

15. The system according to claim 11, wherein determining the one or more parcellations comprises generating a three-dimensional model of the brain from the MRI image, each voxel of the MRI image having an associated identifier.

16. The system according to claim 15, wherein the operations further comprise generating a surface model, the surface model associating a set of RGB values with a coordinate of each voxel, the RGB values reflecting a parcellation of the subject brain, and wherein the one or more surfaces are generated using the surface model.

17. The system according to claim 15, wherein a mapping database associates the identifiers such that each of a plurality of parcellation identifiers matches a mesh identifier in the corresponding three-dimensional location.

18. The system according to claim 11, wherein the three-dimensional coordinates associated with each parcellation are determined based on voxel positions in the MRI data.

19. The system according to claim 11, wherein the corresponding tracts include subsets of tracts of the subject human brain.

20. A method of generating a graphical representation of a network of a subject human brain, comprising:
generating a surface model, the surface model associating a set of RGB values with a coordinate of each voxel, the RGB values reflecting a parcellation of the subject brain, and wherein the one or more surfaces are generated using the surface model;
receiving a first user input to expand a currently available menu option, the currently available menu option for selecting a grouping network of a brain;
determining updated menu data for a menu based on the first user input;
providing the updated menu data for display to a user including at least one grouping option for selecting the grouping network of the subject brain and at least a level one option for selecting a level one network of the subject brain where the grouping network includes the level one network;
receiving, via a user interface, a selection of a network of the subject brain;
determining, based on an MRI image of the subject brain and one or more identifiers associated with the selection, one or more parcellations of the selected network of the subject brain to produce determined parcellations;
determining, using three-dimensional coordinates associated with each determined parcellation, corresponding tracts in a diffusion tensor image of the brain to produce determined tracts, wherein
determining corresponding tracts in a diffusion tensor image of the brain to produce determined tracts comprises:
receiving a tract selection mode indication to select only tracts that: a) begin in one of the determined parcellations and b) end in another one of the determined parcellations; and
responsive to the tract selection mode indication, determining corresponding tracts in a diffusion tensor image of the brain to produce determined tracts that only a) begin in one of the determined parcellations and b) end in another one of the determined parcellations; and
generating a graphical representation of the selected network, the graphical representation including at least one of (i) one or more surfaces representing the one or more determined parcellations, each surface generated using the coordinates, and (ii) the determined tracts.

21. The method of claim 20, wherein the method further comprises
receiving, via the user interface, a first user input;
determining updated menu data for a menu based on the first user input; and forwarding the updated menu data for display to a user including at least one option for selecting the network of the subject brain.

22. The method of claim 21 wherein the method further comprises:
obtaining MRI image data of the subject brain; and
using the MRI image data to construct a mesh model, the surface model and a mapping database for the subject brain, wherein the mesh model provides a three-dimensional location for specified voxels of the MRI image data and assigns a mesh identifier to each specified voxel and wherein the mapping database assigns each specified voxel to a parcellation.

* * * * *